(12) United States Patent
Leu et al.

(10) Patent No.: US 9,023,819 B2
(45) Date of Patent: May 5, 2015

(54) TREATMENT OF A DISEASE OR A CONDITION ASSOCIATED WITH ABERRANT GENE HYPOMETHYLATION BY A METHOD INVOLVING TAILORED EPIGENOMIC MODIFICATION

(75) Inventors: Yu-Wei Leu, Chang Hua (TW); Shu-Huei Hsiao, Chang Hua (TW); Tim Hui-Ming Huang, Columbus, OH (US)

(73) Assignee: National Chung Cheng University, Chia-Yi (TW)

( * ) Notice: Subject to any disclaimer, the term of this patent is extended or adjusted under 35 U.S.C. 154(b) by 1133 days.

(21) Appl. No.: 12/135,565

(22) Filed: Jun. 9, 2008

(65) Prior Publication Data

US 2009/0306191 A1   Dec. 10, 2009

(51) Int. Cl.
*A61K 48/00* (2006.01)
*A61K 31/711* (2006.01)
*A61K 31/713* (2006.01)

(52) U.S. Cl.
CPC ............. *A61K 31/711* (2013.01); *A61K 31/713* (2013.01)

(58) Field of Classification Search
CPC ..................................................... A61K 48/00
See application file for complete search history.

(56) References Cited

U.S. PATENT DOCUMENTS

| | | | |
|---|---|---|---|
| 5,840,497 A | 11/1998 | Holliday | |
| 5,874,416 A | 2/1999 | Sheikhnejad | |
| 6,355,239 B1 | 3/2002 | Bruder et al. | |
| 6,573,099 B2 | 6/2003 | Graham | |
| 7,144,701 B2 * | 12/2006 | Huang | 435/6 |
| 7,316,900 B2 * | 1/2008 | Rabbani et al. | 435/6 |
| 7,427,476 B2 * | 9/2008 | Issa | 435/6.12 |
| 7,498,315 B2 * | 3/2009 | Sheikhnehjad et al. | 514/44 R |
| 2004/0006036 A1 | 1/2004 | Hu et al. | |
| 2005/0196769 A1 | 9/2005 | Fan et al. | |
| 2005/0287668 A1 | 12/2005 | Finney | |

FOREIGN PATENT DOCUMENTS

| | | |
|---|---|---|
| EP | 0707653 | 9/2004 |
| WO | WO 94/29461 | 12/1994 |
| WO | WO 99/24560 | 5/1999 |
| WO | WO 2006/113671 | 10/2006 |
| WO | WO 2007/008252 | 1/2007 |

OTHER PUBLICATIONS

Kannangai et al. Hum Pathol 2007;38:639-44.*
DNA Denaturation, Wikipedia entry, Last updated Jun. 28, 2011.*
Huang et al, FEBS Lett 2011;585:2129-36.*
Zhang et al, CNS & Neurological Disorders—Drug Targets 2013;12:126-41.*
Nebbioso, Mole Oncol 2012;6:657-82.*
Ntziachristos et al., Adv Immunol 2013;117: pp. 1-20.*
Martinez et al. Hum Genet 2013;132:481-93.*
Bird, Adrian "DNA Methylation Patterns and Epigenetic Memory," *Genes & Dev.*, 16:6-21 (2002).
Jones, Peter A. and Stephen B. Baylin, "The Fundamental Role of Epigenetic Events in Cancer," *Nature Reviews*, 3:415-428 (2002).
Nephew, Kenneth P. and Tim Hui-Ming Huang, "Epigenetic Gene Silencing in Cancer Initiation and Progression," *Cancer Letters*, 190:125-133 (2003).
Baylin et al., "Aberrant Patterns of DNA Methylation, Chromatin Formation and Gene Expression in Cancer," *Human Molecular Genetics*, 10(7):687-692 (2001).
Wood et al., "The Genomic Landscapes of Human Breast and Colorectal Cancer," *Science*, 318:1108-1113 (2007).
Leu et al., "Loss of Estrogen Receptor Signaling Triggers Epigenetic Silencing of Downstream Targets in Breast Cancer," *Cancer Reseach*, 64:8184-8192 (2004).
Jin et al., "Identifying Estrogen Receptor α Target Genes Using Integrated Computational Genomics and Chromatin Immunoprecipitation Microarray," *Nucleic Acids Research*, 32(22):6627-6635 (2004).
Yan et al., "Hypermethylation of Ribosomal DNA in Human Breast Carcinoma," *British Journal of Cancer*, 82(3):514-517 (2000).
Weinmann et al., "Isolating Human Transcription Factor Targets by Coupling Chromatin Immunoprecipitation and CpG Island Microarray Analysis," *Genes & Dev.*, 16:235-244 (2002).

* cited by examiner

*Primary Examiner* — Janice Li
(74) *Attorney, Agent, or Firm* — Cesari and McKenna, LLP

(57) ABSTRACT

Disclosed herein is a method for treating a subject having or suspected of having a disease or condition associated with aberrant hypomethylation of one or more genes in the subject, the method involving a tailored epigenomic modification of the subject using methylated polynucleotides directed to hypomethylated genes in the subject.

Also disclosed herein is a medicinal composition for treating a subject having or suspected of having a disease or condition associated with aberrant hypomethylation of one or more genes in the subject, the composition including methylated polynucleotides directed to hypomethylated genes in the subject, so as to result in a tailored epigenomic modification of the subject upon administration.

13 Claims, 5 Drawing Sheets

TREATMENT OF A DISEASE OR A CONDITION ASSOCIATED WITH ABERRANT GENE HYPOMETHYLATION BY A METHOD INVOLVING TAILORED EPIGENOMIC MODIFICATION

BACKGROUND OF THE INVENTION

1. Field of the Invention

This invention relates to a method for treating a subject having or suspected having a disease or condition associated with aberrant hypomethylation of one or more genes in the subject, the method involving a tailored epigenomic modification of the subject using methylated polynucleotides directed to hypomethylated genes in the subject. This invention also relates to a medicinal composition for treating a subject having or suspected of having a disease or condition associated with aberrant hypomethylation of one or more genes in the subject, the composition comprising methylated polynucleotides directed to hypomethylated genes in the subject, so as to result in a tailored epigenomic modification of the subject upon administration.

2. Description of the Related Art

Epigenetics is the study of somatic heritable regulations that modulate gene expression without altering the corresponding DNA sequence. The epigenetic regulation, found to be essential for all the cellular functions, includes a number of processes that modify DNA and histone structures, such as DNA methylation, histone modification and remodeling, as well as gene silencing by small RNAs (H. S. Cho et al. (2007), *Journal of Biochemistry and Molecular Biology*, 40:151-155). The onsets of diseases have been identified to be associated with abnormal epigenetic regulations, which are therefore proposed to be used as detection biomarkers and treatment targets of diseases associated therewith.

DNA methylation, the addition of a methyl group to the fifth carbon position of a cytosine residue by DNA methyltransferase (DNMT), occurs in CpG dinucleotides (A. Bird (2002), *Genes Dev.*, 16:6-21) and is a key epigenetic feature of the human genome. These dinucleotides are usually distributed within stretches of 1- to 2-kb GC-rich DNA, named CpG islands, located in the promoter and/or first exon of 60% of human genes (A. Bird (2002), supra; M. Ehrlich (1982), *Nucleic Acids Res.*, 10:2709-2721). Promoter methylation is known to participate in reorganizing chromatin structure and also plays a role in transcriptional inactivation (A. Bird (2002), supra; M. Ehrlich (2003), *J. Cell Biochem.*, 88:899-910).

Studies have suggested that the CpG island in an active promoter is usually non-methylated, with the surrounding chromatin displaying an "open" configuration, allowing for the access of transcription factors and other co-activators to initiate gene expression (E. Ballestar and M. Esteller (2002), *Carcinogenesis*, 23:1103-1109; P. A. Jones and S. B. Baylin (2002), *Nat. Rev. Genet.*, 3:415-428; K. P. Nephew and Tim H-M Huang (2003), *Cancer Lett.*, 190:125-133). Furthermore, transcription factor occupancy may make the promoter inaccessible to repressors or other chromatin remodeling proteins. In contrast, the CpG islands in an inactive promoter may become methylated, with the associated chromatin exhibiting a "closed" configuration. As a result, the methylated area is no longer accessible to transcription factors, disabling the functional activity of the promoter (P. A. Jones and S. B. Baylin (2002), supra; S. B. Baylin et al. (2001), *Hum. Mol. Genet.*, 10:687-692; M. R. Rountree et al. (2001), *Oncogene*, 20:3156-3165).

Two models have been offered to describe the molecular sequence leading to the establishment of epigenetic gene silencing. One model suggests that histone modifications are the primary initiating event in transient repression (H. Tamaru and E. U. Selker (2001), *Nature* (London), 414:277-283; H. Tamaru et al. (2003), *Nat. Genet.*, 12:177-185). DNA methylation subsequently accumulates in the targeted CpG island, creating a heterochromatin environment to establish a heritable, long-term state of transcriptional silencing. However, a second model suggests that DNA methylation can actually specify unique histone codes for maintaining the silenced state of a gene (S. Eden et al. (1998), *Nature* (London), 394:842; D. Schubeler et al. (2000), *Mol. Cell. Biol.*, 20:9103-9112; J. A. Fahmer et al. (2002), *Cancer Res.*, 62:7213-7218; C. Stirzaker et al. (2004), *Cancer Res.*, 64:3871-3877). Clearly, this epigenetic process is complex and multiple systems may be implemented for genes participating in different signaling pathways.

Accumulating evidence shows that epigenetic modifications have a crucial role in pathological disorders, including, for example, cancer, inherited diseases, and chronic inflammatory diseases. Abnormal DNA methylation is proposed to cause cancer in two major ways, one being the hypermethylation in certain genes especially the tumor suppressor genes, and the other being the global DNA demethylation.

For the treatment of diseases like cancer, chemical demethylation reagents or DNA methyltransferase (DNMT) inhibitors are proposed to restore the expression of tumor suppressor genes. The success in DNA demethylation and restoration of respective gene expression indicate that the epigenetic regulation like DNA methylation is more reversible and feasible than the genetic modification/therapy. While the demethylation agents are easier to be manipulated and bring the high hope for future clinical usage, they gain no control for what genes they are targeting, and uncontrolled demethylation may hurt the cell/individual instead. Therefore, targeted DNA methylation is one step closer for the epigenomic resolution of cancer.

WO 2006/113671 A2 discloses a method of treating a patient having prostate, lung, breast or colon cancer by either administering a demethylating agent to the patient in sufficient amounts to restore expression of a tumor-associated methylation silenced gene in the patient's tumor, or administering to the patient a polynucleotide encoding a polypeptide which is expressed in the patient's tumor thereby restoring expression of the polypeptide in the tumor.

WO 2007/008252 A1 discloses a method of treating cancer or inhibiting tumorigenesis, comprising (1) providing a subject who has, or is at risk for developing, cancer, wherein cells of the subject have a homozygous mutation at nucleotides 178 or 259 of the RB2/p130 gene or have methylation of at least the region from about nucleotide +287 to about +411 of the RB2/p130 gene; and (2) administering an effective amount of a demethylating agent to the subject. In addition, according to WO 2007/008252 A1, compounds such as siRNA and anti-ICBP90 antibodies, which inhibit ICBP90, pRb2/p130 complex or DNA methylase proteins, can be used to treat cancer or inhibit proliferation of tumor cells.

While siRNAs cause gene silencing and are used to treat cancers, siRNAs are expensive and their constructions/designs are more time-consuming. The effective siRNA target sequences are usually different from the sequences that are used to profile the gene's expression. In other words, the profiling means can not be used directly for the interference of the cellular genome. Moreover, not all of the computed siRNA can successfully knockdown the related expression unless they have been tested.

On the other hand, methylated oligonucleotides have been synthesized and used to inhibit the expression of genes. For example, U.S. Pat. No. 5,840,497 issued to Robin Holliday (corresponding to WO 09429461 and EP 0707653 B1) discloses a method for the silencing of specific genes by DNA methylation. The method involves introducing into a cell a single-stranded oligonucleotide containing 5-methyl deoxycytosine, wherein the single-stranded oligonucleotide has a sequence complementary to a sequence within the promoter region of the gene to be silenced, and wherein the sequence within the promoter region contains at least one CpG doublet. In addition, in order to protect the single-stranded oligonucleotide from degradation by nucleases, it is preferred that methylated phosphorothioate oligonucleotides are used. While suggesting the use of methylated oligonucleotides in gene therapy or treatment of certain diseases, the disclosure of U.S. Pat. No. 5,840,497 fails to provide a convincing evidence verifying the effectiveness of methylated oligonucleotides in gene therapy or inherited human diseases.

WO 99/24560 (corresponding to U.S. Pat. No. 5,874,416) discloses a method of inhibiting the expression of a gene in a cell, comprising the step of administering to the cell a single-stranded oligonucleotide comprising nucleotide units wherein at least one cytosine of a cytosine-guanine base pair contains a methyl group in the 5 position of the cytosine nucleotide. In Specific Example 5 of the Specification of WO 99/24560, an in vivo experiment was performed to determine the effect of RZ1X (a 26-mer oligonucleotide with 5-MeC in each of its six CpG sites; see SEQ ID NO: 1) on cell tumorigenicity. However, in said in vivo experiment, MDA-MB 435 cells treated once with 20 mM RZ1X for 4 days were injected into nude mice for the development of tumor. As such, whether or not a methylated oligonucleotide like RZ1X is effective in the treatment of cancers still remains a question.

Diseases like cancer are polygenic and heterogenic in their nature. Therefore, disease themselves vary from person to person and from tissue to tissue. A previous report indicates that there are more than 60 mutations identified in any given breast tumor from any person and these mutations are distributed within 108 signaling pathways (L. D. Wood et al. (2007), *Science*, 318:1108-1113). They are not the mutations in p53 and APC with high occurrence frequency that cause the cancer, but the less frequent, accumulated mutations that really do. Several studies have reported that mutations should lead to more specific, patterned epigenomic mutations, and make the problem even more complicated (Y. W. Leu et al., (2004), *Cancer Res.*, 64:8184-8192; R. Opavsky et al. (2007), *PLoS Genetics*, 3:1757-1769). The complexity of the causes of diseases may lead to a conclusion that it might not be feasible to treat a cancer by targeting a single gene/pathway. Based on this conclusion, the applicants tried to establish a linkage between epigenomic profiling and epigenomic modification so as to switch a cell's fate. Specifically, under the applicants' concept, epigenomic differences within the genome of a subject were comprehensively detected, and these detected differences were subsequently used as a means to conduct a tailored epigenomic modification upon the subject's genome.

Numerous reports indicate that estrogens and estrogen receptors (ERs), ERα and ERβ, play important roles in breast cancer genesis and progression, and tumor ER status is a critical determinant in breast cancer patients to elucidate response to adjuvant treatment with endocrine agent (Y. Kun et al. (2003), *Hum. Mol. Genet.*, 12:3245-3258; R. Schiff et al. (2003), *Clin. Cancer Res.*, 9:447s-454s). ERα functions as a ligand-inducible transcription factor that either up- or down-regulates transcription of various target genes by binding to downstream target gene promoter regions or tethering to other transcription factors, such as AP-1 and SP-1.

In a previous study, the applicants found 70 ERα target loci by the chromatin immunoprecipitation-on-chip (ChIP-on-chip) screening of about 9000 putative GC-rich promoter sequences (Y. W. Leu et al. (2004), supra). Methylation microarray analysis shows that progressive DNA methylation occurs in multiple ERα downstream targets (such as TRIP10, Kr-Znf1, and DCC) in breast cancer genomes. The applicants further used the ChIP-on-chip screening to identify the 70 ERα target loci and found that 27 loci of them were upregulated in ERα-positive (ERα$^+$) human breast cancer cell line MCF-7 than in ERα-negative (ERα$^-$) human breast cancer cell line MDA-MB-231 (V. X. Jin et al. (2004), *Nucleic Acids Res.*, 32:6627-6635). It is well known that patients with ERα$^-$ breast cancer cells suffer greater drug resistance and metastasis, and have lower survival rate than those with ERα$^+$ breast cancer cells.

To test the applicants' concept that detected epigenomic differences within the genome of a subject may be used to conduct a tailored epigenomic modification upon the subject's genome, in the present invention, the applicants conducted epigenomic profiling to determine ERα target genes which were hypomethylated in MDA-MB-231 cells than in MCF7 cells, followed by introducing into MDA-MB-231 cells methylated ERα targets that were synthesized based on the determined hypomethylated ERα target genes. It was found that both the in vitro and in vivo introductions of the methylated ERα targets elevated the methylation status of the ERα target genes in MDA-MB-231 cells, causing the death of MDA-MB-231 cells. Based on the obtained results, it is possible to treat a subject having or suspected of having a disease or condition associated with aberrant hypomethylation of one or more genes using methylated polynucleotides directed to the hypomethylated gene(s) present in the subject's genome.

SUMMARY OF THE INVENTION

Therefore, according to a first aspect, this invention provides a method for treating a subject having or suspected of having a disease or a condition associated with aberrant gene hypomethylation, the subject having normal cells and abnormal cells that arose from the normal cells due to aberrant gene hypomethylation, the abnormal cells having one or more hypomethylated genes determined by comparing methylation profiles of genes in the normal and abnormal cells, each of the hypomethylated genes having a nucleotide sequence including a promoter and a first exon region, the method comprising:

introducing a methylated polynucleotide into the abnormal cells of the subject, the methylated polynucleotide being selected from the group consisting of:
  (i) a single-stranded DNA molecule, which has a nucleotide sequence designed based on a hypomethylated gene in the abnormal cells of the subject, the nucleotide sequence of the single-stranded DNA molecule being identical to or fully complementary to a portion of the nucleotide sequence of the hypomethylated gene at the promoter and/or the first exon region thereof;
  (ii) a double-stranded DNA molecule, one strand of which has a nucleotide sequence designed based on a hypomethylated gene in the abnormal cells of the subject, the nucleotide sequence of said one strand of the double-stranded DNA molecule being identical to or fully complementary to a portion of the nucleotide sequence of the hypomethylated gene at the promoter and/or the first exon region thereof; and (iii) a combination of (i) and (ii), wherein introduction of the methylated polynucleotide causes the hypomethylated gene in the abnormal cells to have a degree of methylation at the promoter and/or the first exon region thereof higher than that before the methylated polynucleotide is introduced into the abnormal cells, thereby causing the expression of the hypomethylated gene to be terminated.

In a second aspect, this invention provides a method for treating a subject having or suspected of having a disease or a condition associated with aberrant gene hypomethylation, the subject having normal cells and abnormal cells that arose from the normal cells due to aberrant hypomethylation of one or more genes, each of the one or more genes having a nucleotide sequence including a promoter and a first exon region, the method comprising:

subjecting the subject to an examination to compare the methylation profile of genes in the normal cells of the subject and that in the abnormal cells of the subject so as to determine which gene is hypomethylated in the abnormal cells of the subject; and introducing a methylated polynucleotide into the abnormal cells of the subject, the methylated polynucleotide being selected from the group consisting of:
  (i) a single-stranded DNA molecule, which has a nucleotide sequence designed based on a hypomethylated gene determined by the examination, the nucleotide sequence of the single-stranded DNA molecule being identical to or fully complementary to a portion of the nucleotide sequence of the hypomethylated gene at the promoter and/or the first exon region thereof;
  (ii) a double-stranded DNA molecule, one strand of which has a nucleotide sequence designed based on a hypomethylated gene determined by the examination, the nucleotide sequence of the one strand of the double-stranded DNA molecule being identical to or fully complementary to a portion of the nucleotide sequence of said hypomethylated gene at the promoter and/or the first exon region thereof; and
  (iii) a combination of (i) and (ii), wherein introduction of the methylated polynucleotide causes the hypomethylated gene in the abnormal cells to have a degree of methylation at the promoter and/or the first exon region thereof higher than that before the methylated polynucleotide is introduced into the abnormal cells, thereby causing the expression of the hypomethylated gene to be terminated.

In a third aspect, this invention provides a medicinal composition for treating a subject having or suspected of having a disease or a condition associated with aberrant gene hypomethylation, the subject having normal cells and abnormal cells that arose from the normal cells due to aberrant gene hypomethylation, the abnormal cells having one or more hypomethylated genes determined by comparing methylation profiles of genes in the normal and abnormal cells, each of the hypomethylated genes having a nucleotide sequence including a promoter and a first exon region, the composition comprising a methylated polynucleotide selected from the group consisting of:
  (i) a single-stranded DNA molecule, which has a nucleotide sequence designed based on a hypomethylated gene in the abnormal cells of the subject, the nucleotide sequence of the single-stranded DNA molecule being identical to or fully complementary to a portion of the nucleotide sequence of the hypomethylated gene at the promoter and/or the first exon region thereof;
  (ii) a double-stranded DNA molecule, one strand of which has a nucleotide sequence designed based on a hypomethylated gene in the abnormal cells of the subject, the nucleotide sequence of the one strand of the double-stranded DNA molecule being identical to or fully complementary to a portion of the nucleotide sequence of the hypomethylated gene at the promoter and/or the first exon region thereof; and
  (iii) a combination of (i) and (ii), whereby introduction of the methylated polynucleotide into the abnormal cells of the subject causes the hypomethylated gene in the abnormal cells of the subject to have a degree of methylation at the promoter and/or the first exon region thereof higher than that before the methylated polynucleotide is introduced into the abnormal cells, thereby causing the expression of the hypomethylated gene to be terminated.

BRIEF DESCRIPTION OF THE DRAWINGS

The above and other features and advantages of the present invention will become apparent in the following detailed description of the preferred embodiments with reference to the accompanying drawing, of which.

DETAILED DESCRIPTION OF THE INVENTION

Figure 1:
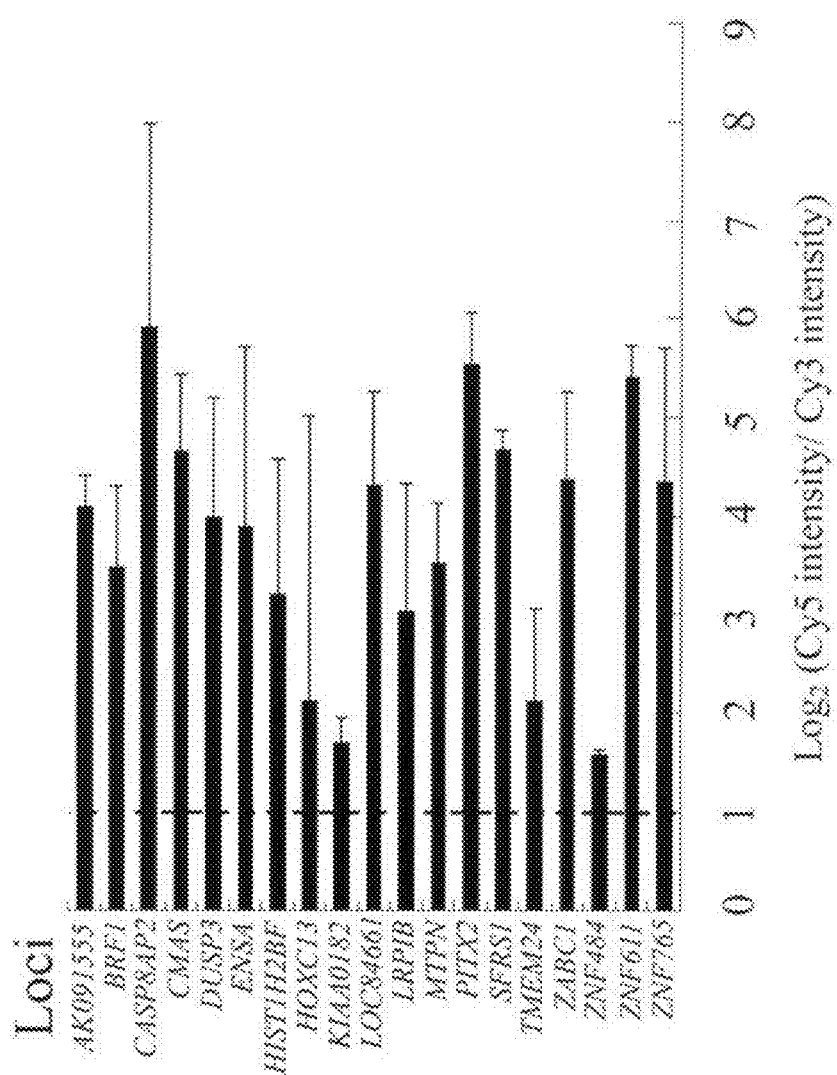
FIG. 1 is a bar diagram showing 19 ERα target loci that were more actively transcribed in ERα⁻ (MDA-MB-231) cells than in ERα⁺ (MCF7) cells as determined by a chromatin immunoprecipitation-on-chip (ChIP-on-chip) assay, wherein the black bars respectively represent the quantification indices for the 19 ERα target loci, the quantification indices being calculated using the equation of $\log_2$ (Cy5 intensity/Cy3 intensity) and expressed as mean±S.D.

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

As used herein, the term "treat" or "treating" refers to reversal, alleviation, relief, improvement or inhibition the progress of, or prevent the disorder or condition to which such term applies, or one or more symptoms of such disorder or condition.

The term "gene" as used herein refers to a DNA sequence, including but not limited to a DNA sequence that can be transcribed into mRNA which can be translated into polypeptide chains, transcribed into rRNA or tRNA or serve as recognition sites for enzymes and other proteins involved in DNA replication, transcription and regulation. This definition includes various sequence polymorphisms, mutations, and/or sequence variants wherein such alterations do not affect the function of the gene product. The term "gene" is intended to include not only regions encoding gene products but also regulatory regions including, e.g., promoters, termination regions, translational regulatory sequences (such as ribosome binding sites and internal ribosome entry sites), enhancers, silencers, insulators, boundary elements, replication origins, matrix attachment sites, and locus control regions. The term "gene" further includes all introns and other DNA sequences spliced from the mRNA transcript, along with variants resulting from alternative splice sites. The term "gene" includes, but is not limited to, structural genes, immunity genes and secretory (transport) genes.

The term "target gene" as used herein refers to a specific gene whose biological function in a cell is the subject to be analyzed. The target gene may be derived from any living or once living prokaryotic or eukaryotic cells, including bacterial cells, yeast cells, fungal cells, plant cells, insect cells and mammalian cells.

The term "promoter" as used herein refers to a DNA regulatory region capable of binding RNA polymerase in a cell and initiating transcription of a downstream (3' direction) coding sequence. The promoter is bound at its 3' terminus by the translation start codon of a coding sequence and extends upstream (5' direction) to include a minimum number of bases or elements necessary to initiate transcription.

The term "exon" as used herein refers to a region of a gene whose nucleotide sequence is transcribed by RNA polymerase and is present in both the primary heteronuclear RNA transcript and the mature messenger RNA. Exons are intermingled with introns, which are non-coding sequences in the DNA and are subsequently eliminated by splicing when the DNA is transcribed into mRNA. Exons are numbered according to the nucleotide position starting from the A in the initiator codon "ATG." An exon may encode part of or all of an expressed protein.

The term "first exon" as used herein refers to the first region of a gene that encodes a polypeptide or a polypeptide region and that is located downstream of the promoter region of the gene.

The term "polynucleotide" as used herein refers to a sequence of nucleotides connected by phosphodiester linkages. A polynucleotide of this invention can be a deoxyribonucleic acid (DNA) molecule or ribonucleic acid (RNA) molecule in either single- or double-stranded form. Nucleotide bases are indicated herein by a single letter code: adenine (A), guanine (G), thymine (T), cytosine (C), inosine (I) and uracil (U). A polynucleotide of this invention can be prepared using standard techniques well known to one of ordinary skill in the art. This term is not to be construed as limiting with respect to the length of a polymer, and encompasses known analogues of natural nucleotides, as well as nucleotides that are modified in the sugar and/or phosphate moieties. This term also encompasses nucleic acids containing modified backbone residues or linkages, which are synthetic, naturally occurring, and non-naturally occurring, which have similar binding properties as the reference nucleic acid, and which are metabolized in a manner similar to the reference nucleotides.

The term "identical to" as used herein refers to two or more nucleotide sequences that are the same when compared and aligned for maximum correspondence, as measured using sequence comparison algorithms or by inspection.

As used herein, the term "complementary to" refers to the ability of two nucleotide sequences to bind sequence-specifically to each other by hydrogen bonding through their purine and/or pyrimidine bases according to the usual Watson-Crick rules for forming duplex nucleic acid complexes.

The term "methylation profile" or "methylation status" when used in this application to describe the state of methylation of a gene, refers to the characteristics of a DNA fragment relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles or the level of gene expression.

The term "hypomethylation" as used herein refers to the methylation state corresponding to a decreased presence of 5-methyl cytosine nucleotide at one or a plurality of CpG dinucleotides within a DNA sequence of a test DNA sample, relative to the amount of 5-methyl cytosine nucleotide found at corresponding CpG dinucleotides within a normal control DNA sample.

The term "hypermethylation" as used herein refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

As used herein, the terms "upstream" and "downstream" refer to the position of an element of nucleotide sequence. "Upstream" signifies an element that is more 5' than the reference element. "Downstream" signifies an element that is more 3' than the reference element.

The term "transfection" as used herein refers to the introduction of an exogenous nucleic acid molecule into a selected host cell. According to techniques known in the art, an exogenous nucleic acid molecule (e.g., a recombinant DNA construct or a recombinant vector) can be introduced into a competent host cell by various techniques, such as gene gun, electroporation, microinjection, heat shock, calcium phosphate precipitation, magnetofection, nucleofection, lipofection, use of transfection reagents, use of cationic polymers, etc.

During normal development, there are clonal discriminations in genomic regulation from tissue to tissue. Also, diseases such as cancer and neurodegeneration are found to arise from various causes and evolved differentially amongst different tissues (like liver and lung) and differently amongst persons. Changes in epigenomic modifications like DNA methylation have been found to be correlated with normal developments and abnormal developments of diseases and are considered to be one of the biomarkers to trace these developments. Since various epigenomic causes can influence these normal and abnormal developments, it is almost impossible to find a single modification that leads to the normal tissue development and to find a cure for all of these diseases and prevent their recurrence.

Cancers are polygenic in their developments. This means that the causes of cancer differ from person to person, from tissue to tissue and even from cell to cell. Also, during chemotherapy for a specific kind of cancer, the treatment usually becomes selection pressure that will force the cancer cells to become resistant and fight for their survival. On the other hand, the non-specific side effects remain a major obstacle for efficient cancer treatment. Therefore, it is highly desired to develop a method that can correctly and precisely engineer target cells and potentially cure the diseases in a tissue- and person-specific way.

In a previous report, the applicants identified 70 estrogen receptor (ER) target loci by ChIP-on-chip assay (Y. W. Leu et al. (2004), supra). ER is a nuclear receptor that binds to its down-stream gene promoter regions and controls their expression. In another previous report, the applicants found that the loss of the up-stream estrogen receptor caused the methylation and therefore silenced the down-stream genes (V. X. Jin et al. (2004), supra). In other words, these 70 loci should be methylated in an ER non-expressing (ERα$^-$) human breast cancer cell line, such as MDA-MB-231, as compared to the ER expressing (ERα$^+$) human breast cancer cell line, MCF7. The majority of the 70 ERα target loci did follow the trend and were hypermethylated, but the applicants found that 19 of them were not. Why do these 19 ERα target genes remain active in ERα$^-$ breast cancer cells?

It is well known that patients with ERα$^-$ breast cancer suffer greater drug resistance and metastasis with lower survival rate than ERα$^+$ patients. With this correlation in mind, the applicants hypothesized that these 19 ERα target genes are essential for the survival of ERα$^-$ cancer cells and are regulated by ER independent signaling pathways. To test this hypothesis, the applicants conducted experiments using methylated PCR products of the promoters and/or first exon regions of these 19 ERα target genes to transfect MDA-MB-231 cells which had greater metastasis ability both in vitro and in vivo. The obtained results reveal that the methylation status of these 19 ERα target genes in transfected MDA-MB-231 cells was elevated, leading to death of the cells.

Based on the obtained results, the applicants combined epigenomics profiling information with epigenomics modifications to create a tool for treatment of diseases, which performs a tailored epigenomic modification upon a subject accepting the treatment.

Accordingly, this invention provides a method for treating a subject having or suspected of having a disease or a condition associated with aberrant gene hypomethylation, the subject having normal cells and abnormal cells that arise from the normal cells due to aberrant gene hypomethylation, the abnormal cells having one or more hypomethylated genes determined by comparing methylation profiles of genes in the normal and abnormal cells, each of the hypomethylated genes having a nucleotide sequence including a promoter and a first exon region, the method comprising:

introducing a methylated polynucleotide into the abnormal cells of the subject, the methylated polynucleotide being selected from the group consisting of:
(i) a single-stranded DNA molecule, which has a nucleotide sequence designed based on a hypomethylated gene in the abnormal cells of the subject, the nucleotide sequence of the single-stranded DNA molecule being identical to or fully complementary to a portion of the nucleotide sequence of the hypomethylated gene at the promoter and/or the first exon region thereof;
(ii) a double-stranded DNA molecule, one strand of which has a nucleotide sequence designed based on a hypomethylated gene in the abnormal cells of the subject, the nucleotide sequence of said one strand of the double-stranded DNA molecule being identical to or fully complementary to a portion of the nucleotide sequence of the hypomethylated gene at the promoter and/or the first exon region thereof; and
(iii) a combination of (i) and (ii), wherein introduction of the methylated polynucleotide causes the hypomethylated gene in the abnormal cells to have a degree of methylation at the promoter and/or the first exon region thereof higher than that before the methylated polynucleotide is introduced into the abnormal cells, thereby causing the expression of the hypomethylated gene to be terminated.

This invention also provides a method for treating a subject having or suspected of having a disease or a condition associated with aberrant gene hypomethylation, the subject having normal cells and abnormal cells that are from the normal cells due to aberrant hypomethylation of one or more genes, each of the one or more genes having a nucleotide sequence including a promoter and a first exon region, the method comprising:

subjecting the subject to an examination to compare the methylation profile of genes in the normal cells of the subject and that in the abnormal cells of the subject so as to determine which gene is hypomethylated in the abnormal cells of the subject; and introducing a methylated polynucleotide into the abnormal cells of the subject, the methylated polynucleotide being selected from the group consisting of:
(i) a single-stranded DNA molecule, which has a nucleotide sequence designed based on a hypomethylated gene determined by the examination, the nucleotide sequence of the single-stranded DNA molecule being identical to or fully complementary to a portion of the nucleotide sequence of the hypomethylated gene at the promoter and/or the first exon region thereof;
(ii) a double-stranded DNA molecule, one strand of which has a nucleotide sequence designed based on a hypomethylated gene determined by the examination, the nucleotide sequence of said one strand of the double-stranded DNA molecule being identical to or fully complementary to a portion of the nucleotide sequence of the hypomethylated gene at the promoter and/or the first exon region thereof; and
(iii) a combination of (i) and (ii), wherein introduction of the methylated polynucleotide causes the hypomethylated gene in the abnormal cells to have a degree of methylation at the promoter and/or the first exon region thereof higher than that before the methylated polynucleotide is introduced into the abnormal cells, thereby causing the expression of the hypomethylated gene to be terminated.

According to this invention, the disease or condition is selected from the group consisting of: cancer, inherited disease, chronic inflammatory disease, autoimmune diseases, and neurodegenerative diseases.

As used herein, the term "cancer" is meant to refer to a persistent neoplasm of any tissue in a biological organism. The neoplasm is characterized as generally malignant or likely to become malignant, potentially invasive, or likely to metastasize to new sites. Representatives of cancer include ovarian cancer, leukemia, lung cancer, colon cancer, CNS cancer, melanoma, renal cancer, prostate cancer, breast cancer, liver cancer, head and neck cancer and the like.

As used herein, the term "inherited disease" refers to a disease or disorder that results from the effect of having defective genes. The disease is inherited genetically because genetic material is accurately copied before being passed onto the offspring from a parent. However, the disease can also arise as a result of a sudden change in the DNA known as a mutation. Common examples of inherited diseases in humans include cystic fibrosis, sickle-cell anemia, polydactyly, Huntingdon's disease, etc.

As used herein, the term "chronic inflammatory disease" refers to diseases or conditions characterized by persistent inflammation in the absence of an identifiable irritant or microbial pathogen, including, e.g., rheumatoid arthritis, psoriasis, cutaneous inflammation, atopic dermatitis, encephalitis, hypersensitivity pneumonitis, chronic lung inflammation, ischemia-reperfusion injury, systemic lupus erythematosus, myositis, ankylosing spondylitis, scleroderma, acute inflammatory demyelinating polyradiculoneuropathy, vasculitis, appendicitis, arachnoiditis, myocarditis, acute cholecystitis, chronic airflow obstruction, chronic hepatitis, chronic obstructive pulmonary disease, conjunctivitis, dermatitis, enteritis, gingivitis, hepatitis, ileitis, asthma, and/or intestinal chronic inflammation diseases such as Crohn's disease, inflammatory bowel disease or ulcerative colitis, transplant rejection, etc.

According to this invention, the hypomethylated gene is one selected from the group consisting of a cancer-associated gene, a gene associated with inherited disease, and a gene associated with chronic inflammatory disease.

In a preferred embodiment of this invention, the hypomethylated gene is a cancer-associated gene, including, but not limited to, AK091555, BRF1, CASP8AP2, CMAS, DUSP3, ENSA, HIST1H2BF, HOXC13, KIAA0182, LOC84661, LRP1B, MTPN, PITX2, SFRS1, TMEM24, ZABC1, ZNF484, ZNF611, ZNF765, and combinations thereof.

In a preferred embodiment of this invention, the methylated polynucleotide is a double-stranded DNA molecule, one strand of which has a nucleotide sequence identical to a portion of the target gene's nucleotide sequence at the promoter thereof.

In another preferred embodiment of this invention, the methylated polynucleotide is a single-stranded DNA molecule, which has a nucleotide sequence identical to a portion of the target gene's nucleotide sequence at the promoter thereof.

According to this invention, the methylated polynucleotide has at least one methylated cytosine nucleotide. The methylated polynucleotide may be methylated at the fifth carbon position of the cytosine nucleotide by the action of DNA methyltransferase or be synthesized chemically or enzymatically. In a preferred embodiment of this invention, the methylated polynucleotide is a PCR-generated fragment using methylated cytosine nucleotide as starting material.

According to this invention, the methylated polynucleotide may have a length ranging from 22 to 2,000 nucleotides or even longer. Preferably, the methylated polynucleotide has a length ranging from 60 to 1,500 nucleotides. More preferably, the methylated polynucleotide has a length ranging from 150 to 1000 nucleotides. In a preferred embodiment of this invention, the methylated polynucleotide has a length of around 500 nucleotides.

According to this invention, any delivery method that could carry DNAs into the cells can be used for delivery of the methylated polynucleotide. For example, the methylated polynucleotide may be introduced into the abnormal cells of the subject via an approach selected from the group consisting of: gene gun, electroporation, microinjection, heat shock, calcium phosphate precipitation, magnetofection, nucleofection, lipofection, use of a transfection reagent, use of a cationic polymer, and combinations thereof.

According to this invention, the methylation profile of genes may be determined by epigenomic detection methods, including, but not limited to, chromatin immunoprecipitation-on-chip (ChIP-on-chip), differential methylation hybridization (DMH), methylation specific digital karyotyping (MSDK), serial analysis of gene expression (SAGE)-based methylation specific digital karyotyping (MSDK), methylation specific PCR, High throughput sequencing, etc.

Details of epigenomic detection methods can be found in various literature, see, e.g. Y. W. Leu et al. (2004), *Cancer Res.*, 64:8184-8192; P. S. Yan et al. (2004), *Br. J. Cancer*, 82:514-5147; P. S. Yan et al. (2002), *Methods Mol Biol.*, 200:87-100; A. S. Weinmann et al. (2002), *Genes Dev.*, 16:235-244; and M. Hu et al. (2006), *Nat. Protoc.*, 1:1621-1636.

According to this invention, the methylated polynucleotide may be administered for therapeutic treatment in any suitable manner, preferably with pharmaceutically acceptable carriers. One skilled in the art will appreciate that suitable methods of administering the methylated polynucleotide are widely available. Pharmaceutically acceptable carriers are also well known to those skilled in the art. The choice of carrier will be determined in part by the particular methylated polynucleotide, as well as by particular methods used to administer medicinal compositions. In practicing the present invention, the methylated polynucleotide can be administered parenterally, for example, by intravenous infusion, orally, topically, intraperitoneally, intravesically or intrathecally.

This invention further provides a medicinal composition for treating a subject having or suspected of having a disease or a condition associated with aberrant gene hypomethylation, the subject having normal cells and abnormal cells that arose from the normal cells due to aberrant gene hypomethylation, the abnormal cells having one or more hypomethylated genes determined by comparing methylation profiles of genes in the normal and abnormal cells, each of the hypomethylated genes having a nucleotide sequence including a promoter and a first exon region, the composition comprising a methylated polynucleotide selected from the group consisting of:

(i) a single-stranded DNA molecule, which has a nucleotide sequence designed based on a hypomethylated gene in the abnormal cells of the subject, the nucleotide sequence of the single-stranded DNA molecule being identical to or fully complementary to a portion of the nucleotide sequence of the hypomethylated gene at the promoter and/or the first exon region thereof;

(ii) a double-stranded DNA molecule, one strand of which has a nucleotide sequence designed based on a hypomethylated gene in the abnormal cells of the subject, the nucleotide sequence of said one strand of the double-stranded DNA molecule being identical to or fully complementary to a portion of the nucleotide sequence of the hypomethylated gene at the promoter and/or the first exon region thereof; and (iii) a combination of (i) and (ii), whereby introduction of the methylated polynucleotide into the abnormal cells of the subject causes the hypomethylated gene in the abnormal cells of the subject to have a degree of methylation at the promoter and/or the first exon region thereof higher than that before the methylated polynucleotide is introduced into the abnormal cells, thereby causing the expression of the hypomethylated gene to be terminated.

The medicinal composition according to this invention can be formulated into a suitable dosage form for parenteral, topical, or oral administration using technology well known to those skilled in the art, which includes, but is not limited to, injections (e.g., sterile aqueous solutions or dispersions), sterile powder, tablets, lozenges, pills, capsules, and the like. In addition, the biologically active components according to this invention can be incorporated into controlled-release drugs and prescriptions.

The dosage and the frequency of introduction of the methylated polynucleotide will vary depending on the following factors: the severity of the disease to be treated, the route of administration, and the weight, age, health condition and response of the subject to be treated.

This invention will be further described by way of the following examples. However, it should be understood that the following examples are solely intended for the purpose of illustration and should not be construed as limiting the invention in practice.

EXAMPLES

Example 1

The Influence of Epigenomic Modification of Estrogen Receptor α (ERα) Target Loci Upon the Cell Fate of Human Breast Cancer Cells Experimental Materials:
1. ERα Non-Expressing (ERα⁻) Human Breast Cancer Cell Line MDA-MB-231:

The MDA-MB-231 cells were maintained in Leibovitz's L-15 medium (Gibco BRL, #11415) supplemented with 10% fetal bovine serum (FBS) (Hyclone, Logan, Utah), 2 mM L-glutamine (Gibco BRL) and 100 mg/mL penicillin/streptomycin, and cultivated in an incubator with culture conditions set at 37° C. and 95% $O_2$/5% $CO_2$. Cell passages were performed when the cell density reached 90% confluence. During passage, the culture medium was removed, and the cells were washed twice with PBS, followed by the addition of 1% trypsin-EDTA so as to detach the cells from the bottom of the petri dish. Thereafter, fresh medium was added to neutralize trypsin's activity, and the medium was repeatedly pipetted using a pipette so as to disperse the detached cells contained therein. The cell suspension thus formed was transferred into a centrifuge tube and then centrifuged at 600 rpm for 5 minutes. After removal of supernatant, fresh medium was added into the centrifuge tube to re-suspend the cell pellet. The resultant cell suspension was dispensed into petri dishes and cultivated in an incubator with culture conditions set at 37° C. and 95% $O_2$/5% $CO_2$.

2. ERα Expressing (ERα⁺) human Breast Cancer Cell Line MCF7:

The MCF7 cells were maintained in Dulbecco's Modified Eagle's Medium (Gibco BRL, #11965) supplemented with 10% FBS (Hyclone, Logan, Utah), 2 mM L-glutamine (Gibco BRL) and 10 mg/mL penicillin/streptomycin, and cultivated in an incubator with culture conditions set at 37° C. and 95% $O_2$/5% $CO_2$. Cell passages were performed in the same way as described above for the MDA-MB-231 cells.

Experimental Procedures:
1. Chromatin Immunoprecipitation on ChIP (Chip-on-Chip) Assay:

The presence of acetylated (at lysine 9) histone 3 (AcH3) components in the promoter region is typically associated with actively transcribed genes. To determine the histone acetylation status of 70 ERα target loci (which were identified in Y. W. Leu et al. (2004), *Cancer Res.*, 64:8184-8192) in the MCF7 and MDA-MB-231 cells, a ChIP-on-chip assay was performed according to the protocols as previously described (Y. W. Leu et al. (2004), supra).

In brief, the 70 ERα target loci were screened from a human CpG island library, which was established by the British Human Genomics Project (now the Sanger Institute, http://www.sangerac.uk/) and contains human CpG loci cloned into the pGEM-5zf(−) vectors (also known as phGMP vectors, Promega, #p2351). The promoter DNAs of these 70 ERα target loci with an averaged size of 0.5 to 1.5 Kbs were spotted onto microarray slides in triplicates (V. X. Jin et al. (2004), *Nucleic Acid Res.*, 32:6627-6635) and used as probes in the assay.

An anti-AcH3 antibody (Upstate, #06-942) was used to immunoprecipitate the AcH3 associated chromatin DNA from the ERα⁻ (MDA-MB-231) cells and ERα⁺ (MCF7) cells. The resultant AcH3 ChIP pull-downs from the MDA-MB-231 and MCF7 cells were labeled with $NH_2$-cyanin 5 (Cy5, Amersham, #PA25001) and $NH_2$-cyanin 3 (Cy3, Amersham, #PA23001), respectively, and co-hybridized onto the microarray slides prepared above. Thereafter, the microarray slides were scanned by a GenePix 4000A scanner (Axon, Union City, Calif.), and the acquired microarray images were quantified and analyzed by GenePix Pro 4.0 software. This ChIP-on-chip assay was conducted twice.

After the Cy5 intensities for the AcH3 ChIP pull-downs from the MDA-MB-231 cells and the Cy3 intensities for the AcH3 ChIP pull-downs from the MCF7 cells were obtained, quantification indices were calculated using the equation of $Log_2$ (Cy5 intensity/Cy3 intensity) so as to quantify the differences of fluorescence intensities between the 2 dyes.

2. Polymerase chain reaction (PCR) amplification of 19 ERα target loci promoters:

19 ERα target loci were identified to be more actively transcribed in MDA-MB-231 cells than in MCF7 cells by the ChIP-on-chip assay. Clones of these 19 ERα target loci were then selected from the human CpG island library and allowed to grow in an ampicillin-containing LB medium. Plasmid DNAs were purified from ampicillin-resistant colonies using the QIAprep Spin Miniprep kit (Qiagen, #27104). The plasmid DNAs thus purified were used as templates in a PCR experiment using the following primers:

hGMP1.1_F primer
5'-cggccgcctgcaggtctgaccataa-3' (SEQ ID NO:1)
hGMP2.1_R primer
5'-aacgcgttgggagctctcccataa-3' (SEQ ID NO:2)

This PCR experiment resulted in the formation of 19 different PCR products, which were purified using the QIAquick PCR clean-up kit (Qiagen, #28104) and used in the following experiments.

3. In Vitro DNA Methylation:

4 μgs of the 19 different PCR products as purified above were respectively methylated by incubation with 20 U CpG methyltransferase (M.SssI)(New England BioLabs, #M0226L) at 37° C. for 4 hours in the presence of 4 μL of 160 μM S-adenosylmethionine (SAM)(New England BioLabs, #M0226L), followed by heating at 65° C. for 5 minutes.

4. Validation of In Vitro DNA Methylation:

The successful induction of DNA methylation was evaluated by two methylation-sensitive restriction enzymes, i.e., HpaII and BstUI. In brief, the 19 methylated PCR products and non-methylated PCR products (not treated with M.SssI, used as control)(each in an amount of 0.4 μg) were respectively incubated with 2 U HpaII (New England Biolabs, #R0171) at 37° C. or with 2 U BstUI (New England Biolabs, #R0518) at 60° C. for 1 hour. The resultant digested products were run in parallel on 6% polyacrylamide gels, followed by staining with ethidium bromide. Thereafter, the polyacrylamide gels were observed under UV light.

5. Transfection:

The 19 valid methylated PCR products (each in an amount of 0.4 μg) were pooled together to form a methylated PCR mix, which was subsequently transfected into the MDA-MB-231 cells using a Fluorescent Arrest-In transfection reagent (FAI, Open Biosystem, #ATR4167) according to the manufacturer's instructions.

In brief, 20 nM of the methylated PCR mix was used to transfect $5\times10^6$ cells in total. Basic Leibovitz's L-15 medium was initially mixed with FAI at room temperature for 10 to 15 minutes. The methylated PCR mix was subsequently added and the resultant mixture was allowed to stand at room temperature for 10 more minutes to form a transfection mixture.

The MDA-MB-231 cells were washed twice with PBS, followed by incubation with the transfection mixture in an incubator with culture conditions set at 37° C. and 95% $O_2$/5% $CO_2$ for 4 hours. Thereafter, Leibovitz's L-15 medium supplemented with 10% FBS was added for subsequent cultivation. The MDA-MB-231 cells were repeatedly subjected to transfection with the methylated PCR mix on Day 0, 2, and 4 to form transfected MDA-MB-231 cells. The fluorescence of FAI was used to evaluate the efficiency of transfection. Almost 100% of the transfected cells showing red fluorescence indicated the success in transfection.

In addition, the MDA-MB-231 cells were transfected with FAI alone and a combination of FAI and the non-methylated PCR mix so as to form the control and mock-transfected MDA-MB-231 cells, respectively.

6. Bisulfite sequencing:

Two days after the third transfection, genomic DNAs were purified from MDA-MB-231 cells transfected with me_ERα targets, the mock-transfected MDA-MB-231 cells and the control cells using QIAamp DNA Mini Kit (Qiagen, #51304), respectively. 0.5 μg of the purified genomic DNA was bisulfite converted using the EZ DNA Methylation kit (Zymo Research, #D5001) according to the manufacturer's instructions. PCR was performed in 25 μL of a reaction mixture containing 2 μL of bisulfite converted genomic DNA (in a total amount of 0.01 μg), 4 μL of primer pair (2.5 μM), 2.5 μL of dNTPs (10 mM), 5 μL of $MgCl_2$ (25 mM), 2.5 μL of 10× Taq buffer, 0.2 μL of Taq DNA polymerase (Fermentus, #EP0402), and 8.8 μL of dd$H_2O$. The primers used in the bisulfite sequencing experiment are listed in Table 1.

TABLE 1

Primers used in the bisulfite sequencing experiment

| Source | Gene | NCBI accession No. | Primer | Sequence (5'→3') |
|---|---|---|---|---|
| Human | CASP8AP2 | NM_012115 | H_CASP8AP2_F | ttttagttatttgggaggttgaggt (SEQ ID NO: 3) |
|  |  |  | H_CASP8AP2_R | accaccacccctaactattttattt (SEQ ID NO: 4) |
| Human | ENSA | NM_207042 | H_ENSA_F | tttttattggttttaggaaggg (SEQ ID NO: 5) |
|  |  |  | H_ENSA_R | tcttcttcttatttctaaaacataac (SEQ ID NO: 6) |

The PCR amplification was performed on a Mastercycler PCR machine (Eppendorf), starting with a 10 min denaturation at 95° C., then running for 40 cycles as follows: 94° C. held for 45 sec for denaturation; ramping down to 54° C. (0.3° C./sec); 54° C. held for 1 min for primer annealing; ramping up to 72° C. (0.3° C./sec); and 72° C. held for 1 min and 15 sec for elongation.

The amplified PCR products were run on an agarose gel, followed by purification using a QIAquick® Gel Extraction Kit (Qiagen, #28704). The purified PCR products were subcloned using the TOPO TA cloning kit (Invitrogen, #K450001). Plasmid DNAs of 10~15 insert-positive clones were isolated by QIAprep Spin Miniprep kit (Qiagen) and sequenced by Trigene Company (Taiwan) using the ABI sequencing system (Applied Biosystems).

7. Semi-Quantitative Methylation-Specific PCR (qMSP):

The targeted DNA methylation was validated by semi-quantitative methylation-specific PCR (qMSP). The qMSP experiment was conducted according to the procedures as described in P. S. Yan et al. (2006), *Clin. Cancer Res.*, 64:6626-6636. The bisulfite-converted genomic DNAs as obtained in the preceding section of "6. Bisulfite sequencing" were used as the template. CpGenome™ Universal Methylated DNA (Chemicon, #S7821) was bisulfite converted as well and used as a positive control.

The qMSP experiment was performed in 25 μL of a reaction mixture containing 2 μL of template (bisulfite converted DNA), 4 μL of primer pair (2.5 μM), 12.5 μL of 2× reaction buffer (SYBR® Green Realtime PCR Master Mix, Toyobo, #QPK201), and 6.5 μL of dd$H_2O$. The primers used in the qMSP experiment are listed in Table 2, in which the primer pair "human H_Col2A1" listed therein was used to amplify the serially diluted (1/10, 1/100 and 1/1000) bisulfite-converted CpGenome Universal Methylated DNA, so as to generate the standard curves for quantification and to normalize the amounts of the methylated DNAs among test samples.

TABLE 2

Primers used in the qMSP experiment

| Source | Gene | NCBI accession No. | Primer | Sequence (5'→3') |
|---|---|---|---|---|
| Human | Col2A1 | NM_033150 | H_Col2A1_F | gggaagatgggatagaagggaatat (SEQ ID NO: 7) |
| | | | H_Col2A1_R | tctaacaattataaactccaaccaccaa (SEQ ID NO: 8) |
| Human | AK091555 | NT_029419.11 | H_AK091555_EXON_MSP_F | ttttagttatgatgtcgaagaggac (SEQ ID NO: 9) |
| | | | H_AK091555_EXON_MSP_R | caaaacacactactaactaaccgac (SEQ ID NO: 10) |
| Human | BRF1 | NM_001519 | H_BRF1_EXON_MSP_F | ttttaaattttagtttcgggttgc (SEQ ID NO: 11) |
| | | | H_BRF1_EXON_MSP_R | gaacgaactaacctcccttacg (SEQ ID NO: 12) |
| | | | H_BRF1_PROMOTER_MSP_F | tttacgggtaattataggtggttac (SEQ ID NO: 13) |
| | | | H_BRF1_PROMOTER_MSP_R | ccgaactctaaaaataataaacgaa (SEQ ID NO: 14) |
| Human | CASP8AP2 | NM_012115 | H_CASP8AP2_PROMOTER_MSP_F | aataaaatagttaggggtggtggtc (SEQ ID NO: 15) |
| | | | H_CASP8AP2_PROMOTER_MSP_R | ttcaaacaaaatatcgctttatcgc (SEQ ID NO: 16) |
| Human | CMAS | NM_018686 | H_CMAS_PROMOTER_MSP_F | agagaatgtgagggaaattttatc (SEQ ID NO: 17) |
| | | | H_CMAS_PROMOTER_MSP_R | actaatcacctctaatataaccgac (SEQ ID NO: 18) |
| Human | DUSP3 | NM_004090 | H_DUSP3_EXON_MSP_F | aggattttgagattttagggc (SEQ ID NO: 19) |
| | | | H_DUSP3_EXON_MSP_R | actccgaaaactacgaaacg (SEQ ID NO: 20) |
| | | | H_DUSP3_PROMOTER_MSP_F | gtggtgttttattgtagggagtc (SEQ ID NO: 21) |
| | | | H_DUSP3_PROMOTER_MSP_R | tacaaaacccaataaacatttcgta (SEQ ID NO: 22) |
| Human | ENSA | NM_207042 | H_ENSA_PROMOTER_MSP_F | ttattatgttggttaggttggtttc (SEQ ID NO: 23) |
| | | | H_ENSA_PROMOTER_MSP_R | tacaatttaacatttcctaaacgtc (SEQ ID NO: 24) |
| Human | HIST1H2BF | NM_003522 | H_HIST1H2BF_EXON_MSP_F | tttcgtttggcgtattataataagc (SEQ ID NO: 25) |
| | | | H_HIST1H2BF_EXON_MSP_R | ccttaataccctctaacacgacgta (SEQ ID NO: 26) |
| Human | HOXC13 | NM_017410 | H_HOXC13_EXON_MSP_F | ttttttttaggtaaggaagggattc (SEQ ID NO: 27) |
| | | | H_HOXC13_EXON_MSP_R | caaacgacgaaaataattaaaacg (SEQ ID NO: 28) |
| Human | KIAA0182 | NM_014615 | H_KIAA0182_EXON_MSP_F | gtagtttagataaatattgggcgac (SEQ ID NO: 29) |
| | | | H_KIAA0182_EXON_MSP_R | cgaacttacaaaaaaacaatacgat (SEQ ID NO: 30) |

TABLE 2-continued

Primers used in the qMSP experiment

| Source Gene | NCBI accession No. | Primer | Sequence (5'→3') |
|---|---|---|---|
| | | H_KIAA0182_PROMOTER_MSP_F | taaattatagcgttcggttaaggtc (SEQ ID NO: 31) |
| | | H_KIAA0182_PROMOTER_MSP_R | gaaccgttactaactcctacctacg (SEQ ID NO: 32) |
| Human LOC84661 | NM_032574 | H_LOC84661_PROMOTER_MSP_F | gttagattttggttaggatttacgc (SEQ ID NO: 33) |
| | | H_LOC84661_PROMOTER_MSP_R | gtaaataacgactatcgcacgac (SEQ ID NO: 34) |
| Human LRP1B | NM_018557 | H_LRP1B_EXON_MSP_F | gtcgttcgattttaggttttaagc (SEQ ID NO: 35) |
| | | H_LRP1B_EXON_MSP_R | cgaaaaatattctccttacctcg (SEQ ID NO: 36) |
| Human MTPN | NM_145808 | H_MTPN_EXON_MSP_F | cggtagtttgtatattgcgtatgc (SEQ ID NO: 37) |
| | | H_MTPN_EXON_MSP_R | aaaattcttttacgaccaccga (SEQ ID NO: 38) |
| Human PITX2 | NM_000325 | H_PITX2_PROMOTER_MSP_F | tattttgggttcgtattaaaagtc (SEQ ID NO: 39) |
| | | H_PITX2_PROMOTER_MSP_R | gaactactacctcgccgtacg (SEQ ID NO: 40) |
| Human SFRS1 | NM_006924 | H_SFRS1_EXON_MSP_F | agattttattttggagaaatcga (SEQ ID NO: 41) |
| | | H_SFRS1_EXON_MSP_R | ttcccaacttaaaataatttacgaa (SEQ ID NO: 42) |
| Human TMEM24 | NM_014807 | H_TMEM24_PROMOTER_MSP_F | tttaggaaatgggaagttagaagtc (SEQ ID NO: 43) |
| | | H_TMEM24_PROMOTER_MSP_R | tattaaatttccacaaatcgaacg (SEQ ID NO: 44) |
| Human ZABC1 | NM_006526 | H_ZABC1_EXON_MSP_F | gggtaagaagggagtatcgataac (SEQ ID NO: 45) |
| | | H_ZABC1_EXON_MSP_R | tactaaataacttaaaatccgcgtc (SEQ ID NO: 46) |
| Human ZNF484 | NM_031488 | H_ZNF484_EXON_MSP_F | ttgagtatgcgtaaatttaggtagc (SEQ ID NO: 47) |
| | | H_ZNF484_EXON_MSP_R | caaaacaataatcatttacctcgaa (SEQ ID NO: 48) |
| Human ZNF611 | NM_030972 | H_ZNF611_EXON_MSP_F | gttgggattataggtttgagttatc (SEQ ID NO: 49) |
| | | H_ZNF611_EXON_MSP_R | acaattttatatatatacattatccttcgt (SEQ ID NO: 50) |
| Human ZNF765 | NM_001040185 | H_ZNF765_PROMOTER_MSP_F | tatttttcgttggtttgagtatttc (SEQ ID NO: 51) |
| | | H_ZNF765_PROMOTER_MSP_R | accctacctaaataaaacgtacgat (SEQ ID NO: 52) |

The qMSP experiment was performed on a Bio-Rad iQ5 real time PCR machine, starting with a 7 min and 30 sec denaturation at 95° C., then running for 45 cycles as follows: 95° C. held for 30 sec and 60° C. held for 1 min. For melting curve validation, PCR was performed at the following conditions: 55° C. held for 1 min and 30 sec, and then ramping up to 95° C. (0.5° C./30 sec). The presence of a single melting peak confirmed the generation of a single PCR product.

The methylation percentage was calculated by the following equation:

$$A = (B/C) \times 100$$

in which:
A: Methylation percentage (%)
B: Intensity of amplifications by an ERα target gene primer pair used in the qMSP experiment.
C: Intensity of amplifications by the human H_Col2A1 primer pair In addition, the methylation percentage of the promoter or first exon region of an ERα target gene in the mock-transfected cells was set as 100%, and the methylation percentage of the promoter or first exon region of the ERα target gene in cells transfected with me_ERα targets was normalized by that of the mock transfected cells.

8. Morphological Comparison of MDA-MB-231 Cells Transfected with me_ERα targets and the mock-transfected MDA-MB-231 cells:

Two days after the third transfection, the morphologies of MDA-MB-231 cells transfected with me_ERα targets versus the mock-transfected MDA-MB-231 cells were observed by an optical microscope.

Results:

In this Example, the applicants tried to prove that the cell fate of MDA-MB-231 cells could be switched by conducting epigenomic modifications based on the epigenomic profiling information of the cells.

If an active chromatin component like AcH3 was detected by e.g., the ChIP-on-chip assay, genes associated therewith should be more actively transcribed than the non-associated ones. To test the hypothesis that most of the ER regulated genes were silenced in ERα⁻ cells, the histone acetylation status of 70 ERα target loci as previously identified (Y. W. Leu et al. (2004), supra) were analyzed by a ChIP-on-chip assay.

Referring to FIG. 1, all the quantification indices of the 19 ERα target loci were larger than 1, indicating that the promoters of these 19 ERα target loci were associated with AcH3 and more actively transcribed in MDA-MB-231 cells than in MCF7 cells.

Figure 2:
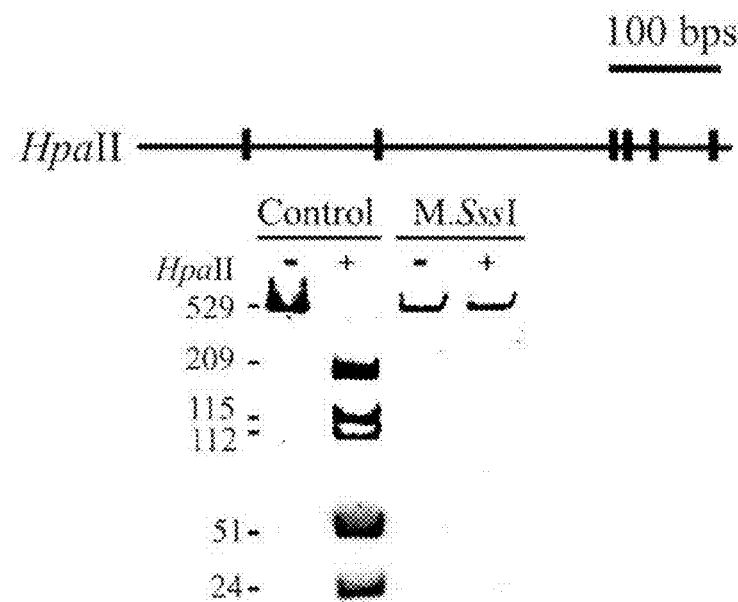
FIG. 2 shows the HpaII restriction map of the ENSA promoter (upper) and the polyacrylamide gel electrophoresis image (lower) of the methylated PCR product and non-methylated PCR product (control) of the ENSA promoter after HpaII restriction treatment, in which the symbols "−" and "+" represent "no HpaII treatment" and "with HpaII treatment", respectively, and the numerals indicate the sizes of the HpaII-digested DNA fragments in bps.
Figure 3:
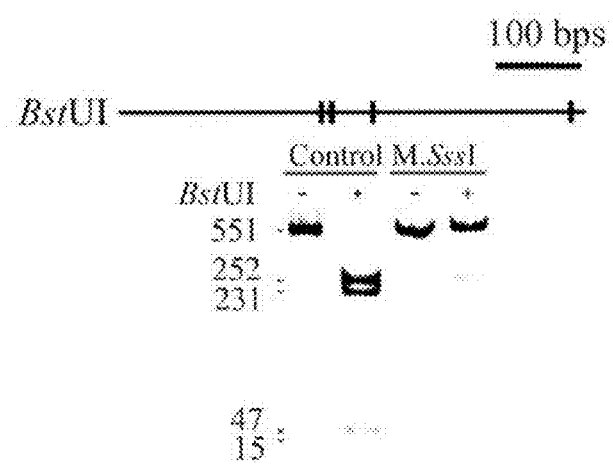
FIG. 3 shows the BstUI restriction map of the HOXC13 promoter (upper) and the polyacrylamide gel electrophoresis image (lower) of the methylated PCR product and non-methylated PCR product (control) of the HOXC13 promoter after BstUI restriction treatment, in which the symbols "−" and "+" represent "no BstUI treatment" and "with BstUI treatment", respectively, and the numerals indicate the sizes of the BstUI-digested DNA fragments in bps.

The applicants further cloned the 19 ERα target loci and used the same to prepare 19 different methylated PCR products. The successful induction of DNA methylation was evaluated by two methylation-sensitive restriction enzymes, HpaII and BstUI, which acted at the non-methylated CCGG sequence and CGCG sequence, respectively. Representative results of the 19 different methylated PCR products are shown in FIGS. 2 and 3, in which the methylated PCR products of the ENSA promoter and the HOXC13 promoter were treated with HpaII and BstUI, respectively.

The ENSA and HOXC13 genes were sensitive to the restriction enzyme treatment prior to M.SssI treatment. It can be seen from FIG. 2 that in the control group (without M.SssI treatment), incubation with HpaII digested the non-methylated PCR products of the ENSA promoter into small fragments, indicating that the CpG sites in the promoter region of the ENSA gene were non-methylated. After treatment with M.SssI, an enzyme that triggers the methylation in vitro, the non-methylated PCR products of the ENSA promoter were no longer digested by HpaII. The results confirmed that using M.SssI treatment, the CpG sites were converted into methylated state. Similar results were observed for the methylated PCR products of the HOXC13 promoter when treated with BstUI (see FIG. 3).

The 19 valid methylated PCR products were then pooled together to form a methylated PCR mix, which was used to transfect MDA-MB-231 cells. The applicants found that the methylated PCR mix could induce methylation of the promoters and/or first exon regions of the 19 ERα target loci in MDA-MB-231 cells, as proved by the bisulfite sequencing experiments (FIGS. 4 and 5) and the semi-quantitative methylation-specific PCR (qMSP) experiments (FIG. 6).

Figure 4:
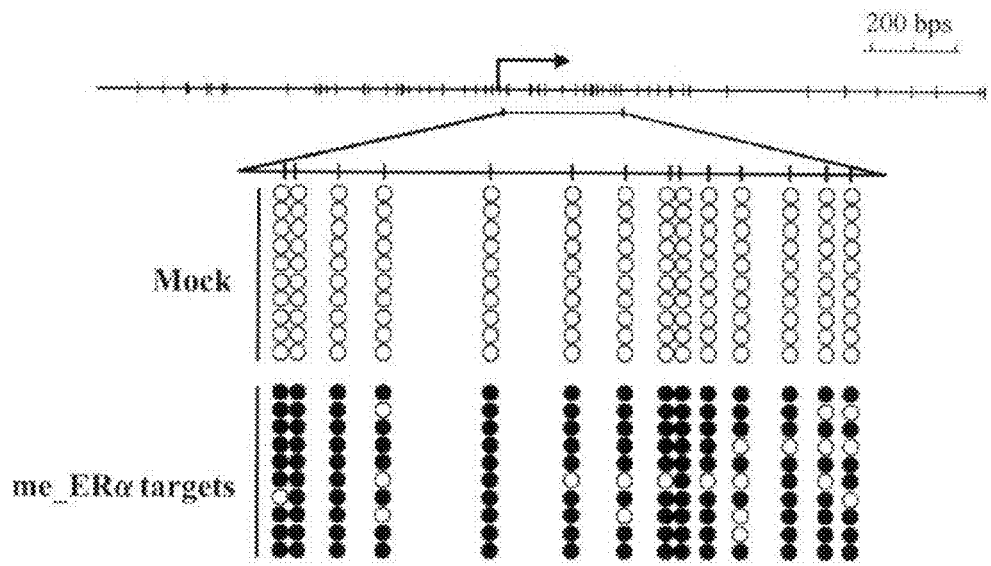
FIG. 4 shows the bisulfite sequencing results of the first exon region of the CASP8AP2 gene in MDA-MB-231 cells transfected with methylated ERα targets (me_ERα targets) versus the mock-transfected MDA-MB-231 cells, in which filled and open circles indicate methylated CpG dinucleotides and non-methylated CpG dinucleotides, respectively, and the bent arrow indicates the transcriptional start site.
Figure 5:
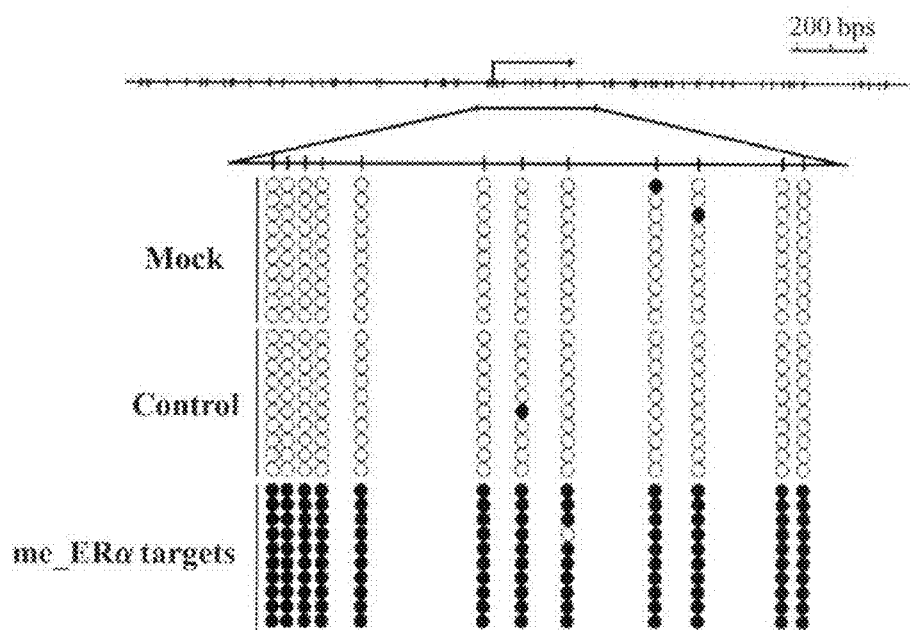
FIG. 5 shows the bisulfite sequencing results of the promoter and first exon region of the ENSA gene in MDA-MB-231 cells transfected with me_ERα targets versus the mock-transfected MDA-MB-231 cells and the control cells, in which filled and open circles indicate methylated CpG dinucleotides and non-methylated CpG dinucleotides, respectively, and the bent arrow indicates the transcriptional start site.

FIG. 4 shows the bisulfite sequencing results of the first exon region of the CASP8AP2 gene, whereas FIG. 5 shows the bisulfite sequencing results of the promoter and the first exon region of the ENSA gene. It can be seen from FIGS. 4 and 5 that most CpG dinucleotides in the first exon region of the CASP8AP2 gene and in the promoter and the first exon region of the ENSA gene were non-methylated (open circles) in the mock-transfected MDA-MB-231 cells and/or control cells. After introduction of the in vitro methylated DNAs, endogenous DNA methylation (filled circles) was efficiently induced in MDA-MB-231 cells transfected with me_ERα targets.

Figure 6:
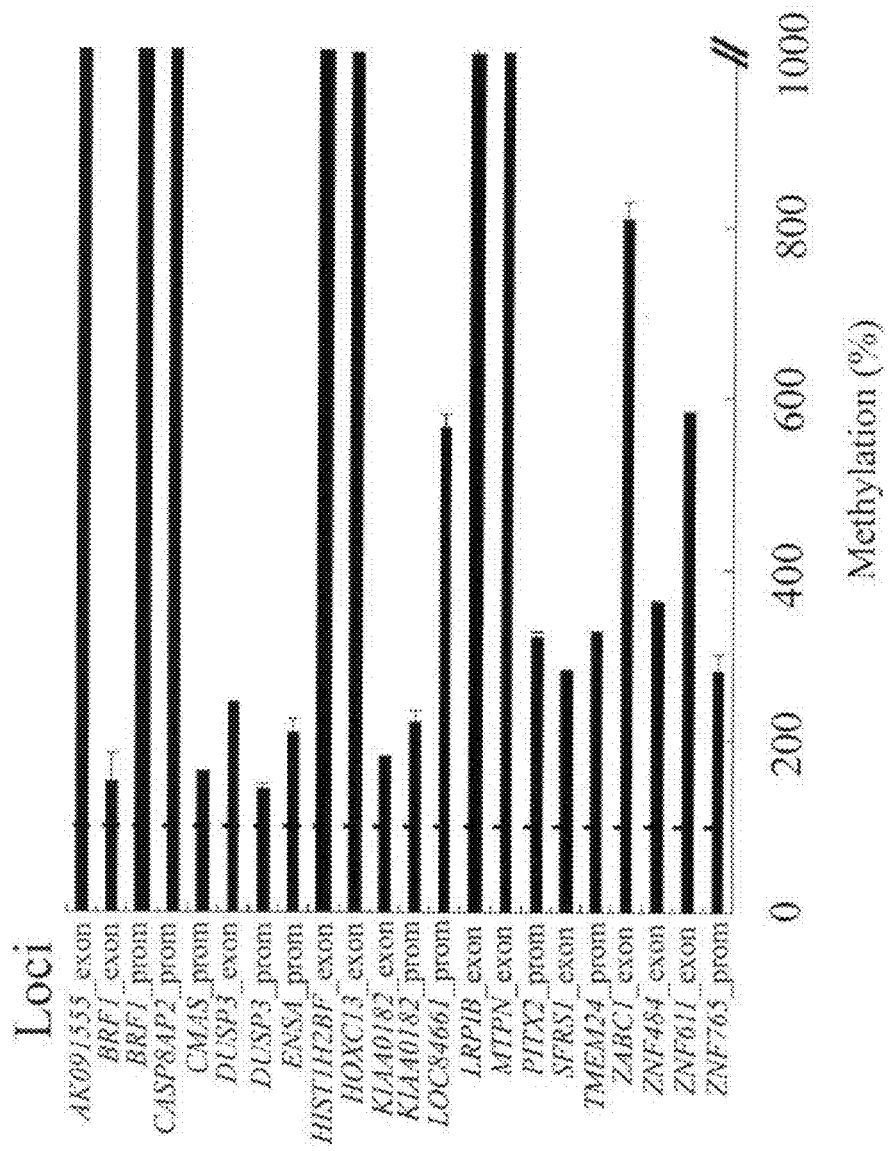
FIG. 6 is a bar diagram showing the methylation extents of 19 ERα target loci in MDA-MB-231 cells transfected with me_ERα targets as determined by semi-quantitative methylation-specific PCR (qMSP)

FIG. 6 shows the methylation extents of the 19 ERα target loci in MDA-MB-231 cells transfected with me_ERα targets as determined by the qMSP experiment. It can be seen from FIG. 6 that the methylation levels of the 19 ERα target loci at the promoter or the first exon region thereof were increased by 1.5 to more than 10 folds in MDA-MB-231 cells transfected with me_ERα targets than in the mock-transfected MDA-MB-231 cells.

Figure 7:
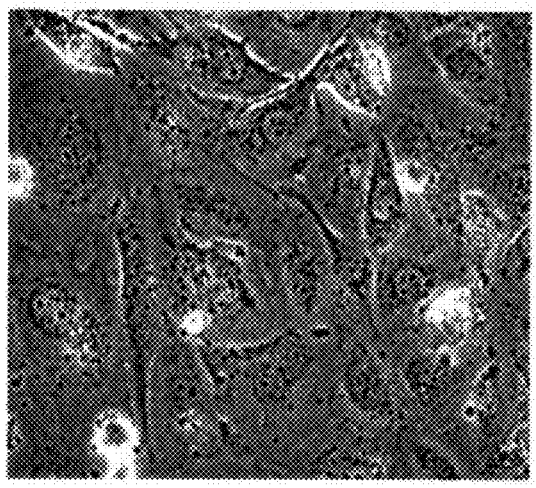
FIG. 7 shows the morphological changes of MDA-MB-231 cells transfected with me_ERα targets versus the mock-transfected MDA-MB-231 cells two days after the third transfection.
Figure 7:
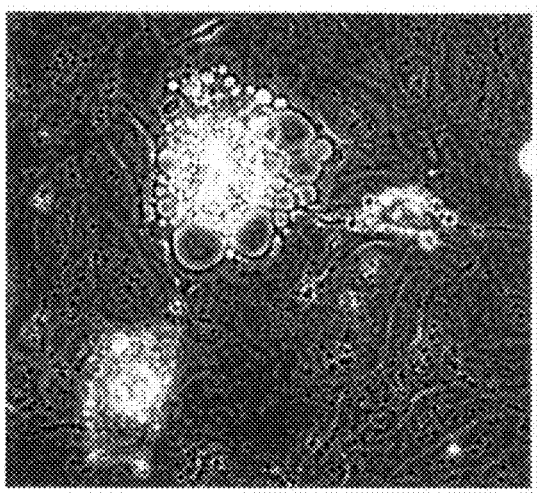

The morphological changes between MDA-MB-231 cells transfected with me_ERα targets and the mock-transfected MDA-MB-231 cells were also observed. As can be seen from FIG. 7, the mock-transfection itself does not affect the cell viability. Massive cell death was found when the 19 methylated ERα targets were pooled together and transfected into MDA-MB-231 cells. The simultaneous suppression of the 19 ERα target loci resulted in the death of MDA-MB-231 cells transfected with me_ERα targets.

Example 2

In Vivo Anti-Cancer Effect of the In Vitro Methylated ENSA Promoter DNA

In order to characterize the in vivo effect and efficiency of the in vitro methylated ENSA promoter DNA, 6 week-old nude mice (NarI:ICR-Foxn1$^{nu}$) were used as the animal model.

Firstly, the nude mice were subcutaneously injected with 1×10$^7$ MDA-MB-231 cells suspended in 100 μL of 1×PBS. After the solid tumors with size of 0.5 cm in diameter were formed (about 6 weeks after the injection), 4 μg of the methylated PCR product of the ENSA promoter as obtained in the section of "3. In vitro DNA methylation" of Example 1 was denatured and mixed with in vivo-jetPEI™ transfection reagent (Polyplus-transfection, #201) according to the manufacturer's instructions, followed by subcutaneous injection into the already grown solid tumor once a week. The solid tumor size was measured using a micrometer and the treatment underwent a period of at least four months. The control group were nude mice injected with the in vivo-jetPEI™ transfection reagent only.

MDA-MB-231 cells are very aggressive and their metastasis ability is high so that the tumor usually expands once it grows in nude mice. The nude mice of the control group were not able to survive to the time four months after the first injection of in vivo-jetPEI™ transfection reagent.

In contrast, the original solid tumor became softer two days after the initial injection of the methylated PCR product of the ENSA promoter, and necrosis-like tumor cells could be sucked out by needle five days after the injection. A concave was then formed at the injection site and the tumor was confined without further expansion. Wherever the injection is, the tumor growth would be abolished. The treated nude mice were able to survive for more than four months after the first injection of methylated PCR product of the ENSA promoter.

In addition, 4 mM of methylated ENSA oligos with the same sequences of SEQ ID NO:23 and SEQ ID NO:24 were also used to evaluate the in vivo anticancer effect thereof according to the above protocol except for the denaturation procedure. As expected, similar results were obtained.

In conclusion, the applicants have developed a tailored DNA methylation method that translates the detected epigenomic differences into tools for manipulation of the cell fate, such as killing the cancer cells. Based on the gained epigenomics knowledge and profiling results, the probes on the array can be used directly as the modification agents after in vitro methylation. The targeting of several genes at the same time might be able to prevent the further evolution of the cancer epigenome. Since there are epigenomic differences from person to person and from tissue to tissue, a platform that combines epigenomic profiling information with epigenomic modifications will make the tailored, personalized therapy easier.

Most of the current genetic manipulation/therapy is done by delivering and inserting a permanent trans-gene into cells. The insertion itself could suffer from possible positional effects and the trans-genes are mostly non-reversible in nature if inserted into the genome, both limiting the clinical applications. In contrast, this invention delivers a short-term epigenomic modification which is heritable through somatic cells. The epigenomic modification itself is reversible by current developed drugs and encounters less positional effects, since the modification does not insert any trans-genes into the genome. Ideally, if the epigenomic profiling is comprehensive and sufficient to tell the epigenomic differences between target cells and surrounding cells, the chosen targets loci will affect only the targeted cells but not the surrounding cells. Cell type specific targeting will then be expected. Application of this invention will follow the developmental path of siRNA but will be easier, less cost, and more reliable. In the long run, this invention might be considered as a powerful tool for gene therapy.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. A method for treating a subject having or suspected of having breast cancer associated with aberrant gene hypomethylation in estrogen receptor (ER) non-expressing cancer cells, the subject having normal cells and ER non-expressing cancer cells that arose from the normal cells due to aberrant hypomethylation of one or more genes, each of the one or more genes having a nucleotide sequence including a promoter and a first exon region, the method comprising:
   subjecting the subject to an examination to compare the methylation profile of genes in the normal cells of the subject and that in the ER non-expressing cancer cells of the subject so as to determine which gene is hypomethylated in the ER non-expressing cancer cells of the subject; and
   introducing a methylated polynucleotide into the ER non-expressing cancer cells of the subject, the methylated polynucleotide being selected from the group consisting of:
   (i) a single-stranded DNA molecule, which has a nucleotide sequence designed based on a hypomethylated gene determined by the examination, the nucleotide sequence of the single-stranded DNA molecule being identical to or fully complementary to a portion of the nucleotide sequence of the hypomethylated gene at the promoter and/or the first exon region thereof, wherein the hypomethylated gene is the endosulfine alpha gene (ENSA);
   (ii) a double-stranded DNA molecule, one strand of which has a nucleotide sequence designed based on a hypomethylated gene determined by the examination, the nucleotide sequence of said one strand of the double-stranded DNA molecule being identical to or fully complementary to a portion of the nucleotide sequence of the hypomethylated gene at the promoter and/or the first exon region thereof, wherein the hypomethylated gene is ENSA; and
   (iii) a combination of (i) and (ii),
wherein introduction of the methylated polynucleotide causes the hypomethylated gene in the ER non-expressing cancer cells to have a degree of methylation at the promoter and/or the first exon region thereof higher than that before the methylated polynucleotide is introduced into the ER non-expressing cancer cells, thereby causing the expression of the hypomethylated gene to be terminated.

2. The method as claimed in claim 1, wherein the methylated polynucleotide is a double-stranded DNA molecule, one strand of which has a nucleotide sequence identical to a portion of the nucleotide sequence of the hypomethylated gene at the promoter and/or the first exon region thereof.

3. The method as claimed in claim 1, wherein the methylated polynucleotide has at least one methylated cytosine nucleotide.

4. The method as claimed in claim 1, wherein the methylated polynucleotide has a length ranging from 22 to 2000 nucleotides.

5. The method as claimed in claim 4, wherein the examination includes an epigenomic detection method selected from the group consisting of chromatin immunoprecipitation-on-chip (ChIP-on-chip), differential methylation hybridization (DMH), methylation specific digital karyotyping (MSDK), serial analysis of gene expression (SAGE)-based methylation specific digital karyotyping (MSDK), methylation specific PCR, high throughput sequencing, and combinations thereof.

6. The method as claimed in claim 1, wherein introducing the methylated polynucleotide into the ER non-expressing cancer cells of the subject is conducted via an approach selected from the group consisting of: gene gun, electroporation, microinjection, heat shock, calcium phosphate precipitation, magnetofection, nucleofection, lipofection, use of a transfection reagent, use of a cationic polymer, and combinations thereof.

7. A method for treating a subject having or suspected of having breast cancer associated with aberrant gene hypomethylation in estrogen receptor (ER) non-expressing cancer cells, the subject having normal cells and ER non-expressing cancer cells that arose from the normal cells due to aberrant gene hypomethylation, the ER non-expressing cancer cells having one or more hypomethylated genes determined by comparing methylation profiles of genes in the normal and ER non-expressing cancer cells, each of the hypomethylated genes having a nucleotide sequence including a promoter and a first exon region, the method comprising:
   introducing a methylated polynucleotide into the ER non-expressing cancer cells of the subject, the methylated polynucleotide being selected from the group consisting of:
   (i) a single-stranded DNA molecule, which has a nucleotide sequence designed based on a hypomethylated gene in the ER non-expressing cancer cells of the subject, the nucleotide sequence of the single-stranded DNA molecule being identical to or fully complementary to a portion of the nucleotide sequence of the hypomethylated gene at the promoter and/or the first exon region thereof, wherein the hypomethylated gene is the endosulfine alpha gene (ENSA);
   (ii) a double-stranded DNA molecule, one strand of which has a nucleotide sequence designed based on a hypomethylated gene in the ER non-expressing cancer cells of the subject, the nucleotide sequence of said one strand of the double-stranded DNA molecule being identical to or fully complementary to a portion of the nucleotide sequence of the hypomethylated gene at the promoter and/or the first exon region thereof, wherein the hypomethylated gene is ENSA; and
   (iii) a combination of (i) and (ii),
wherein introduction of the methylated polynucleotide causes the hypomethylated gene in the ER non-expressing cancer cells to have a degree of methylation at the promoter and/or the first exon region thereof higher than that before the methylated polynucleotide is introduced into the ER non-expressing cancer cells, thereby causing the expression of the hypomethylated gene to be terminated.

8. The method as claimed in claim 7, wherein the methylated polynucleotide is a double-stranded DNA molecule, one strand of which has a nucleotide sequence identical to a portion of the nucleotide sequence of the hypomethylated gene at the promoter and/or the first exon region thereof.

9. The method as claimed in claim 7, wherein the methylated polynucleotide is a single-stranded DNA molecule, which has a nucleotide sequence identical to a portion of the nucleotide sequence of the hypomethylated gene at the promoter and/or the first exon region thereof.

10. The method as claimed in claim 7, wherein the methylated polynucleotide has at least one methylated cytosine nucleotide.

11. The method as claimed in claim 7, wherein the methylated polynucleotide has a length ranging from 22 to 2000 nucleotides.

12. The method as claimed in claim 7, wherein comparing methylation profiles of genes in the normal and ER non-expressing cancer cells is conducted by an epigenomic detection method selected from the group consisting of chromatin immunoprecipitation-on-chip (ChIP-on-chip), differential methylation hybridization (DMH), methylation specific digital karyotyping (MSDK), serial analysis of gene expression (SAGE)-based methylation specific digital karyotyping (MSDK), methylation specific PCR, high throughput sequencing, and combinations thereof.

13. The method as claimed in claim 7, wherein introducing the methylated polynucleotide into the ER non-expressing cancer cells of the subject is conducted via an approach selected from the group consisting of gene gun, electroporation, microinjection, heat shock, calcium phosphate precipitation, magnetofection, nucleofection, lipofection, use of a transfection reagent, use of a cationic polymer, and combinations thereof.

* * * * *

SEQUENCE LISTING

```
<160> NUMBER OF SEQ ID NOS: 52

<210> SEQ ID NO 1
<211> LENGTH: 25
<212> TYPE: DNA
<213> ORGANISM: Artificial
<220> FEATURE:
<223> OTHER INFORMATION: Forward primer hGMP1.1_F for PCR

<400> SEQUENCE: 1
cggccgcctg caggtctgac cataa                                          25

<210> SEQ ID NO 2
<211> LENGTH: 24
<212> TYPE: DNA
<213> ORGANISM: Artificial
<220> FEATURE:
<223> OTHER INFORMATION: Reverse primer hGMP2.1_R for PCR

<400> SEQUENCE: 2
aacgcgttgg gagctctccc ataa                                           24

<210> SEQ ID NO 3
<211> LENGTH: 25
<212> TYPE: DNA
<213> ORGANISM: Artificial
<220> FEATURE:
<223> OTHER INFORMATION: Forward primer H_CASP8AP2_F for bisulfite
      sequencing of human CASP8AP2 gene

<400> SEQUENCE: 3
ttttagttat ttgggaggtt gaggt                                          25

<210> SEQ ID NO 4
<211> LENGTH: 25
<212> TYPE: DNA
<213> ORGANISM: Artificial
<220> FEATURE:
<223> OTHER INFORMATION: Reverse primer H_CASP8AP2_R for bisulfite
``` sequencing of human CASP8AP2 gene

<400> SEQUENCE: 4
accaccaccc ctaactattt tattt                                              25

<210> SEQ ID NO 5
<211> LENGTH: 23
<212> TYPE: DNA
<213> ORGANISM: Artificial
<220> FEATURE:
<223> OTHER INFORMATION: Forward primer H_ENSA_F for bisulfite
      sequencing of human ENSA gene

<400> SEQUENCE: 5
tttttattgg tttttaggaa ggg                                                23

<210> SEQ ID NO 6
<211> LENGTH: 26
<212> TYPE: DNA
<213> ORGANISM: Artificial
<220> FEATURE:
<223> OTHER INFORMATION: Reverse primer H_ENSA_R for bisulfite
      sequencing of human ENSA gene

<400> SEQUENCE: 6
tcttcttctt atttctaaaa cataac                                             26

<210> SEQ ID NO 7
<211> LENGTH: 25
<212> TYPE: DNA
<213> ORGANISM: Artificial
<220> FEATURE:
<223> OTHER INFORMATION: Forward primer H_Col2A1_F for qMSP of human
      Col2A1 gene

<400> SEQUENCE: 7
gggaagatgg gatagaaggg aatat                                              25

<210> SEQ ID NO 8
<211> LENGTH: 28
<212> TYPE: DNA
<213> ORGANISM: Artificial
<220> FEATURE:
<223> OTHER INFORMATION: Reverse primer H_Col2A1_R for qMSP of human
      Col2A1 gene

<400> SEQUENCE: 8
tctaacaatt ataaactcca accaccaa                                           28

<210> SEQ ID NO 9
<211> LENGTH: 25
<212> TYPE: DNA
<213> ORGANISM: Artificial
<220> FEATURE:
<223> OTHER INFORMATION: Forward primer H_AK091555_EXON_MSP_F for qMSP
      of human AK091555 gene

<400> SEQUENCE: 9
ttttagttat gatgtcgaag aggac                                              25

<210> SEQ ID NO 10
<211> LENGTH: 25
<212> TYPE: DNA
<213> ORGANISM: Artificial
<220> FEATURE:
<223> OTHER INFORMATION: Reverse primer H_AK091555_EXON_MSP_R for qMSP
      of human AK091555 gene

<400> SEQUENCE: 10
caaaacacac tactaactaa ccgac         25

<210> SEQ ID NO 11
<211> LENGTH: 24
<212> TYPE: DNA
<213> ORGANISM: Artificial
<220> FEATURE:
<223> OTHER INFORMATION: Forward primer H_BRF1_EXON_MSP_F for qMSP of
      human BRF1 gene

<400> SEQUENCE: 11 tttttaaattt tagtttcggg ttgc          24

<210> SEQ ID NO 12
<211> LENGTH: 22
<212> TYPE: DNA
<213> ORGANISM: Artificial
<220> FEATURE:
<223> OTHER INFORMATION: Reverse primer H_BRF1_EXON_MSP_R for qMSP of
      human BRF1 gene

<400> SEQUENCE: 12
gaacgaacta acctccctta cg             22

<210> SEQ ID NO 13
<211> LENGTH: 25
<212> TYPE: DNA
<213> ORGANISM: Artificial
<220> FEATURE:
<223> OTHER INFORMATION: Forward primer H_BRF1_PROMOTER_MSP_F for qMSP
      of human BRF1 gene

<400> SEQUENCE: 13
tttacgggta attataggtg gttac          25

<210> SEQ ID NO 14
<211> LENGTH: 25
<212> TYPE: DNA
<213> ORGANISM: Artificial
<220> FEATURE:
<223> OTHER INFORMATION: Reverse primer H_BRF1_PROMOTER_MSP_R for qMSP
      of human BRF1 gene

<400> SEQUENCE: 14
ccgaactcta aaataataa acgaa           25

<210> SEQ ID NO 15
<211> LENGTH: 25
<212> TYPE: DNA
<213> ORGANISM: Artificial
<220> FEATURE:
<223> OTHER INFORMATION: Forward primer H_CASP8AP2_PROMOTER_MSP_F for
      qMSP of human CASP8AP2 gene

<400> SEQUENCE: 15
aataaaatag ttagggttgg tggtc          25

<210> SEQ ID NO 16
<211> LENGTH: 25
<212> TYPE: DNA
<213> ORGANISM: Artificial
<220> FEATURE:
<223> OTHER INFORMATION: Reverse primer H_CASP8AP2_PROMOTER_MSP_R for
      qMSP of human CASP8AP2 gene

<400> SEQUENCE: 16
ttcaaacaaa atatcgcttt atcgc                                       25

<210> SEQ ID NO 17
<211> LENGTH: 25
<212> TYPE: DNA
<213> ORGANISM: Artificial
<220> FEATURE:
<223> OTHER INFORMATION: Forward primer H_CMAS_PROMOTER_MSP_F for qMSP
      of human CMAS gene

<400> SEQUENCE: 17
agagaatgtg agggaaattt ttatc                                       25

<210> SEQ ID NO 18
<211> LENGTH: 25
<212> TYPE: DNA
<213> ORGANISM: Artificial
<220> FEATURE:
<223> OTHER INFORMATION: Reverse primer H_CMAS_PROMOTER_MSP_R for qMSP
      of human CMAS gene

<400> SEQUENCE: 18
actaatcacc tctaatataa ccgac                                       25

<210> SEQ ID NO 19
<211> LENGTH: 22
<212> TYPE: DNA
<213> ORGANISM: Artificial
<220> FEATURE:
<223> OTHER INFORMATION: Forward primer H_DUSP3_EXON_MSP_F for qMSP of
      human DUSP3 gene

<400> SEQUENCE: 19
aggatttttg agattttagg gc                                          22

<210> SEQ ID NO 20
<211> LENGTH: 20
<212> TYPE: DNA
<213> ORGANISM: Artificial
<220> FEATURE:
<223> OTHER INFORMATION: Reverse primer H_DUSP3_EXON_MSP_R for qMSP of
      human DUSP3 gene

<400> SEQUENCE: 20
actccgaaaa ctacgaaacg                                             20

<210> SEQ ID NO 21
<211> LENGTH: 24
<212> TYPE: DNA
<213> ORGANISM: Artificial
<220> FEATURE:
<223> OTHER INFORMATION: Forward primer H_DUSP3_PROMOTER_MSP_F for qMSP
      of human DUSP3 gene

<400> SEQUENCE: 21
gtggtgtttt tattgtaggg agtc                                        24

<210> SEQ ID NO 22
<211> LENGTH: 25
<212> TYPE: DNA
<213> ORGANISM: Artificial
<220> FEATURE:
<223> OTHER INFORMATION: Reverse primer H_DUSP3_PROMOTER_MSP_R for qMSP
      of human DUSP3 gene

<400> SEQUENCE: 22
tacaaaaccc aataaacatt tcgta                                              25

<210> SEQ ID NO 23
<211> LENGTH: 25
<212> TYPE: DNA
<213> ORGANISM: Artificial
<220> FEATURE:
<223> OTHER INFORMATION: Forward primer H_ENSA_PROMOTER_MSP_F for qMSP
      of human ENSA gene

<400> SEQUENCE: 23
ttattatgtt ggttaggttg gtttc                                              25

<210> SEQ ID NO 24
<211> LENGTH: 25
<212> TYPE: DNA
<213> ORGANISM: Artificial
<220> FEATURE:
<223> OTHER INFORMATION: Reverse primer H_ENSA_PROMOTER_MSP_R for qMSP
      of human ENSA gene

<400> SEQUENCE: 24
tacaatttaa catttcctaa acgtc                                              25

<210> SEQ ID NO 25
<211> LENGTH: 25
<212> TYPE: DNA
<213> ORGANISM: Artificial
<220> FEATURE:
<223> OTHER INFORMATION: Forward primer H_HIST1H2BF_EXON_MSP_F for qMSP
      of human HIST1H2BF gene

<400> SEQUENCE: 25
tttcgtttgg cgtattataa taagc                                              25

<210> SEQ ID NO 26
<211> LENGTH: 25
<212> TYPE: DNA
<213> ORGANISM: Artificial
<220> FEATURE:
<223> OTHER INFORMATION: Reverse primer H_HIST1H2BF_EXON_MSP_R for qMSP
      of human HIST1H2BF gene

<400> SEQUENCE: 26
ccttaatacc ctctaacacg acgta                                              25

<210> SEQ ID NO 27
<211> LENGTH: 25
<212> TYPE: DNA
<213> ORGANISM: Artificial
<220> FEATURE:
<223> OTHER INFORMATION: Forward primer H_HOXC13_EXON_MSP_F for qMSP of
      human HOXC13 gene

<400> SEQUENCE: 27 tttttttag gtaaggaagg gattc                                               25

<210> SEQ ID NO 28
<211> LENGTH: 24
<212> TYPE: DNA
<213> ORGANISM: Artificial
<220> FEATURE:
<223> OTHER INFORMATION: Reverse primer H_HOXC13_EXON_MSP_R for qMSP of
      human HOXC13 gene

<400> SEQUENCE: 28
caaacgacga aaataattaa aacg                                          24

<210> SEQ ID NO 29
<211> LENGTH: 25
<212> TYPE: DNA
<213> ORGANISM: Artificial
<220> FEATURE:
<223> OTHER INFORMATION: Forward primer H_KIAA0182_EXON_MSP_F for qMSP
      of human KIAA0182 gene

<400> SEQUENCE: 29
gtagtttaga taaatattgg gcgac                                         25

<210> SEQ ID NO 30
<211> LENGTH: 25
<212> TYPE: DNA
<213> ORGANISM: Artificial
<220> FEATURE:
<223> OTHER INFORMATION: Reverse primer H_KIAA0182_EXON_MSP_R for qMSP
      of human KIAA0182 gene

<400> SEQUENCE: 30
cgaacttaca aaaaacaat acgat                                          25

<210> SEQ ID NO 31
<211> LENGTH: 25
<212> TYPE: DNA
<213> ORGANISM: Artificial
<220> FEATURE:
<223> OTHER INFORMATION: Forward primer H_KIAA0182_PROMOTER_MSP_F for
      qMSP of human KIAA0182 gene

<400> SEQUENCE: 31
taaattatag cgttcggtta aggtc                                         25

<210> SEQ ID NO 32
<211> LENGTH: 25
<212> TYPE: DNA
<213> ORGANISM: Artificial
<220> FEATURE:
<223> OTHER INFORMATION: Reverse primer H_KIAA0182_PROMOTER_MSP_R for
      qMSP of human KIAA0182 gene

<400> SEQUENCE: 32
gaaccgttac taactcctac ctacg                                         25

<210> SEQ ID NO 33
<211> LENGTH: 25
<212> TYPE: DNA
<213> ORGANISM: Artificial
<220> FEATURE:
<223> OTHER INFORMATION: Forward primer H_LOC84661_PROMOTER_MSP_F for
      qMSP of human LOC84661 gene

<400> SEQUENCE: 33
gttagatttt ggttaggatt tacgc                                         25

<210> SEQ ID NO 34
<211> LENGTH: 23
<212> TYPE: DNA
<213> ORGANISM: Artificial
<220> FEATURE:
<223> OTHER INFORMATION: Reverse primer H_LOC84661_PROMOTER_MSP_R for
      qMSP of human LOC84661 gene

<400> SEQUENCE: 34
gtaaataacg actatcgcac gac                                           23

<210> SEQ ID NO 35
<211> LENGTH: 24
<212> TYPE: DNA
<213> ORGANISM: Artificial
<220> FEATURE:
<223> OTHER INFORMATION: Forward primer H_LRP1B_EXON_MSP_F for qMSP of
      human LRP1B gene

<400> SEQUENCE: 35
gtcgttcgat tttaggtttt aagc                                          24

<210> SEQ ID NO 36
<211> LENGTH: 24
<212> TYPE: DNA
<213> ORGANISM: Artificial
<220> FEATURE:
<223> OTHER INFORMATION: Reverse primer H_LRP1B_EXON_MSP_R for qMSP of
      human LRP1B gene

<400> SEQUENCE: 36
cgaaaaaata ttctccttac ctcg                                          24

<210> SEQ ID NO 37
<211> LENGTH: 24
<212> TYPE: DNA
<213> ORGANISM: Artificial
<220> FEATURE:
<223> OTHER INFORMATION: Forward primer H_MTPN_EXON_MSP_F for qMSP of
      human MTPN gene

<400> SEQUENCE: 37
cggtagtttg tatattgcgt atgc                                          24

<210> SEQ ID NO 38
<211> LENGTH: 22
<212> TYPE: DNA
<213> ORGANISM: Artificial
<220> FEATURE:
<223> OTHER INFORMATION: Reverse primer H_MTPN_EXON_MSP_R for qMSP of
      human MTPN gene

<400> SEQUENCE: 38
aaaattcttt tacgaccacc ga                                            22

<210> SEQ ID NO 39
<211> LENGTH: 25
<212> TYPE: DNA
<213> ORGANISM: Artificial
<220> FEATURE:
<223> OTHER INFORMATION: Forward primer H_PITX2_PROMOTER_MSP_F for qMSP
      of human PITX2 gene

<400> SEQUENCE: 39
tatttttggg ttcgtattaa aagtc                                         25

<210> SEQ ID NO 40
<211> LENGTH: 21
<212> TYPE: DNA
<213> ORGANISM: Artificial
<220> FEATURE:
<223> OTHER INFORMATION: Reverse primer H_PITX2_PROMOTER_MSP_R for qMSP
      of human PITX2 gene

<400> SEQUENCE: 40
gaactactac ctcgccgtac g                                             21

<210> SEQ ID NO 41
<211> LENGTH: 25
<212> TYPE: DNA
<213> ORGANISM: Artificial
<220> FEATURE:
<223> OTHER INFORMATION: Forward primer H_SFRS1_EXON_MSP_F for qMSP of
      human SFRS1 gene

<400> SEQUENCE: 41
agatttttat ttttggagaa atcga                                         25

<210> SEQ ID NO 42
<211> LENGTH: 25
<212> TYPE: DNA
<213> ORGANISM: Artificial
<220> FEATURE:
<223> OTHER INFORMATION: Reverse primer H_SFRS1_EXON_MSP_R for qMSP of
      human SFRS1 gene

<400> SEQUENCE: 42
ttcccaactt aaataattt acgaa                                          25

<210> SEQ ID NO 43
<211> LENGTH: 25
<212> TYPE: DNA
<213> ORGANISM: Artificial
<220> FEATURE:
<223> OTHER INFORMATION: Forward primer H_TMEM24_PROMOTER_MSP_F for qMSP
      of human TMEM24 gene

<400> SEQUENCE: 43
tttaggaaat gggaagttag aagtc                                         25

<210> SEQ ID NO 44
<211> LENGTH: 24
<212> TYPE: DNA
<213> ORGANISM: Artificial
<220> FEATURE:
<223> OTHER INFORMATION: Reverse primer H_TMEM24_PROMOTER_MSP_R for qMSP
      of human TMEM24 gene

<400> SEQUENCE: 44
tattaaattt ccacaaatcg aacg                                          24

<210> SEQ ID NO 45
<211> LENGTH: 24
<212> TYPE: DNA
<213> ORGANISM: Artificial
<220> FEATURE:
<223> OTHER INFORMATION: Forward primer H_ZABC1_EXON_MSP_F for qMSP of
      human ZABC1 gene

<400> SEQUENCE: 45
gggtaagaag ggagtatcga taac                                          24

<210> SEQ ID NO 46
<211> LENGTH: 25
<212> TYPE: DNA
<213> ORGANISM: Artificial
<220> FEATURE:
<223> OTHER INFORMATION: Reverse primer H_ZABC1_EXON_MSP_R for qMSP of
      human ZABC1 gene

<400> SEQUENCE: 46
tactaaataa cttaaaatcc gcgtc                                         25

```
<210> SEQ ID NO 47
<211> LENGTH: 25
<212> TYPE: DNA
<213> ORGANISM: Artificial
<220> FEATURE:
<223> OTHER INFORMATION: Forward primer H_ZNF484_EXON_MSP_F for qMSP of
      human ZNF484 gene

<400> SEQUENCE: 47
ttgagtatgc gtaaatttag gtagc                                          25

<210> SEQ ID NO 48
<211> LENGTH: 25
<212> TYPE: DNA
<213> ORGANISM: Artificial
<220> FEATURE:
<223> OTHER INFORMATION: Reverse primer H_ZNF484_EXON_MSP_R for qMSP of
      human ZNF484 gene

<400> SEQUENCE: 48
caaaacaata atcatttacc tcgaa                                          25

<210> SEQ ID NO 49
<211> LENGTH: 25
<212> TYPE: DNA
<213> ORGANISM: Artificial
<220> FEATURE:
<223> OTHER INFORMATION: Forward primer H_ZNF611_EXON_MSP_F for qMSP of
      human ZNF611 gene

<400> SEQUENCE: 49
gttgggatta taggtttgag ttatc                                          25

<210> SEQ ID NO 50
<211> LENGTH: 30
<212> TYPE: DNA
<213> ORGANISM: Artificial
<220> FEATURE:
<223> OTHER INFORMATION: Reverse primer H_ZNF611_EXON_MSP_R for qMSP of
      human ZNF611 gene

<400> SEQUENCE: 50
acaattttat atatatacat tatccttcgt                                     30

<210> SEQ ID NO 51
<211> LENGTH: 25
<212> TYPE: DNA
<213> ORGANISM: Artificial
<220> FEATURE:
<223> OTHER INFORMATION: Forward primer H_ZNF765_PROMOTER_MSP_F for qMSP
      of human ZNF765 gene

<400> SEQUENCE: 51 tattttttcgt tggtttgagt atttc                                         25

<210> SEQ ID NO 52
<211> LENGTH: 25
<212> TYPE: DNA
<213> ORGANISM: Artificial
<220> FEATURE:
<223> OTHER INFORMATION: Reverse primer H_ZNF765_PROMOTER_MSP_R for qMSP
      of human ZNF765 gene

<400> SEQUENCE: 52
accctaccta aataaaacgt acgat                                          25
```